US009993006B2

(12) United States Patent
Bruck et al.

(10) Patent No.: US 9,993,006 B2
(45) Date of Patent: Jun. 12, 2018

(54) BIOLOGICALS AND THEIR USE IN PLANTS

(71) Applicants: PIONEER HI-BRED INTERNATIONAL, INC., Johnston, IA (US); E I DU PONT DE NEMOURS AND COMPANY, Wilmington, DE (US)

(72) Inventors: Denny Joseph Bruck, Johnston, IA (US); Frederick C Burns, II, Grimes, IA (US); James Kevin Presnail, St Louis, MO (US)

(73) Assignees: PIONEER HI-BRED INTERNATIONAL, INC.IA (US); E I DU PONT DE NEMOURS AND COMPANY, Wilmington, DE (US)

( * ) Notice: Subject to any disclaimer, the term of this patent is extended or adjusted under 35 U.S.C. 154(b) by 0 days. days.

(21) Appl. No.: 15/287,860

(22) Filed: Oct. 7, 2016

(65) Prior Publication Data

US 2017/0099844 A1 Apr. 13, 2017

Related U.S. Application Data

(60) Provisional application No. 62/240,138, filed on Oct. 12, 2015.

(51) Int. Cl.

| | |
|---|---|
| ***A01N 63/04*** | (2006.01) |
| ***A01N 25/00*** | (2006.01) |
| ***A01N 63/00*** | (2006.01) |
| ***A01N 25/30*** | (2006.01) |
| ***A01N 43/36*** | (2006.01) |
| ***A01N 43/78*** | (2006.01) |
| ***A01N 43/54*** | (2006.01) |

(52) U.S. Cl.

CPC ............. *A01N 63/04* (2013.01); *A01N 25/00* (2013.01); *A01N 25/30* (2013.01); *A01N 43/36* (2013.01); *A01N 43/54* (2013.01); *A01N 43/78* (2013.01); *A01N 63/00* (2013.01)

(58) Field of Classification Search

CPC ........ A01N 63/04; A01N 43/78; A01N 43/36; A01N 43/54; A01N 25/00; A01N 63/00; A01N 25/30

See application file for complete search history.

(56) References Cited

U.S. PATENT DOCUMENTS

| | | | |
|---|---|---|---|
| 7,790,151 | B1 | 9/2010 | Raina et al. |
| 2011/0038839 | A1 | 2/2011 | Jackson et al. |
| 2013/0156740 | A1 | 6/2013 | Leland |
| 2015/0282490 | A1 | 10/2015 | Wachendorff-Neumann et al. |

FOREIGN PATENT DOCUMENTS

| | | | |
|---|---|---|---|
| EP | 2078746 | A1 | 7/2009 |
| WO | 2003038065 | A1 | 8/2003 |
| WO | 2014117118 | A1 | 7/2014 |
| WO | 2015069708 | A1 | 5/2015 |
| WO | 2016055913 | | 2/2016 |
| WO | 2017-049355 | A1 | 3/2017 |

OTHER PUBLICATIONS

Kabaluk, J.T., Metarhizium anisopliae Seed Treatment Increases Yield of Field Corn When Applied for Wireworm Control, 2007, Agronomy Journal, vol. 99, Issue 5, pp. 1377-1381.*

Nguyen, et al . "Biocontrol Potential of Metarhizium anisopliae and Beauveria bassiana Against Diamondback Moth, *Plutella xylostella*", Omonrice, vol. 15: 86-93 (2007).

Tiago, et al., "Biological insect control using Metarhizium anisopliae: morphological, molecular, and ecological aspects", Ciencia Rural, Santa Maria, vol. 44, N. 4: 645-651 (2014).

Manisegaran et al. "Field Evaluation of Metarhizium anisopliae (Metschnikoff) Sorokin against Holotrichia serrata Blanch) in sugarcane", Journal of Biopesticides, vol. 4(2): 190-193 (2011).

Zimmerman et al., "The Entomopathogenic Fungus *Metarhizium anisopliae* and its Potential as Biocontrol Agent", Pestic. Sci., vol. 37: 375-379 (1993).

International Search Report for International Application No. PCT/US2016/055952 dated Feb. 1, 2017.

US Environmental Protection Agency Registration Action Document , "Metarhizium anisopliae strain F52".

Kepler et al, "Community composition and population genetics of insect pathogenic fungi in the genus *Metarhizium* from soils of a long-term agricultural research system", Environmental Microbiology, 17(8): 2791-2804 (2015).

Zhang et al, "Genome Studies on Nematophagous and Entomogenous Fungi in China", Journal of Fungi, 2(9): 1-14 (2016).

Hoffman et al, "Effects of Entomopathogens on Mortality of Western Corn Rootworm (*Coleoptera*: Chrysomelidae) and Fitness Costs of Resistance to Cry3Bb1 Maize", Journal Economic Etonmology, 107(1): 352-360 (2014).

Rudeen et al, "Entomopathogenic fungi in cornfields and their potential to manage larval western corn rootworm *Diabrotica virgifera virgifera*", Journal of Invertebrate Pathology, 114: 329-332 (2013).

Petzold-Maxwell et al, "Interactions Among Bt Maize, Entomoathogens and Rootworm Species (*Coleoptera*: Chrysomelidae) in the Field: Effects on Survival, Yield and Root Injury", Biological and Microbial Control, 106(2): 622-632 (2013).

Keyser et al, "Metarhizium seed treatment mediates fungal dispersal via roots and induces infections in insects", Fungal Ecology II, pp. 122-131 (2014).

Sasan et al, "The Insect-Pathogenic Fungus *Metarhizium robertsii* (Clavicipitaceae) is also an Endophyte that Stimulates Plant Root Development", American Journal of Botany, 99(1): 101-107 (2012).

Wyrebek, et al, "Three sympatrically occurring species of *Metarhizium* show plant rhizosphere specificity", Microbiology, 157:2904-2911 (2011).

Pava-Ripoll et al, "The rhizosphere-competent entomopathogen Metarhizium anisopliae expresses a specific subset genes in plant root exudate", Microbiology, 157: 47-55 (2011).

(Continued)

*Primary Examiner* — John Pak
*Assistant Examiner* — Andriae M. Holt

(57) ABSTRACT

Entomopathogenic fungal strains, compositions, and methods of using the strains for reducing overall insect damage.

28 Claims, 1 Drawing Sheet

(56) References Cited

OTHER PUBLICATIONS

Scheepmaker et al, "Natural and released incoculum levels of entomopathogenic fungal biocontrol agents in soil in relation to risk assessment and in accordance with EU regulations", Biocontrol and Technology, 20(5): 503-552 (2010).
Krueger et al, "Soil Treatment with Entomopathogenic Fungi for Corn Rootworm (*Diabrotica* spp.) Larval Control", Biological Control, 9: 67-74 (1997).
Liao et al, "The plant beneficial effects of *Metarhizium* species correlate with their association with roots", Applied Genetics and Molecular Biotechnology, 98: 7089-7096 (2014).
Meissle et al, "Susceptibility of Diabrotica virgifera virgifera (Coleoptera: Chrysomelidae) to Entomopathogenic Fungus *Metarhizium anisopliae* when Feeding on Bacillus thuringiensis Cry3Bb1-Expressing Maize", Applied and Environmental Microbiology, 75(12): 3937-3943 (2009).
Petzold-Maxwell, et al, "Tritophic interaction among Bt maize, an insect pest and entomopathogens: effects on development and survival of western corn rootworm", Annals of Applied Biology, 160: 43-55 (2011).
Behle et al, Efficacy of a Granular Formulation containing Metarhizium brunneum F52 (Hypocreales: Clavicipitaceae) Microsderotia Against Nymphs of Ixodes Scapularis (Acari: Ixoididae), J Econ Entomol. Feb. 2013;106(1):57-63).
Fischhoff IR, Keesing F, Osffeld RS (2017) The tick biocontrol agent Metarhizium brunneum (= M. anisopliae) (strain F52) does not reduce non-target arthropods. PLOS ONE 12(11): e0187675. https://doi.org/10.1371/journal.pone.0187675.

* cited by examiner

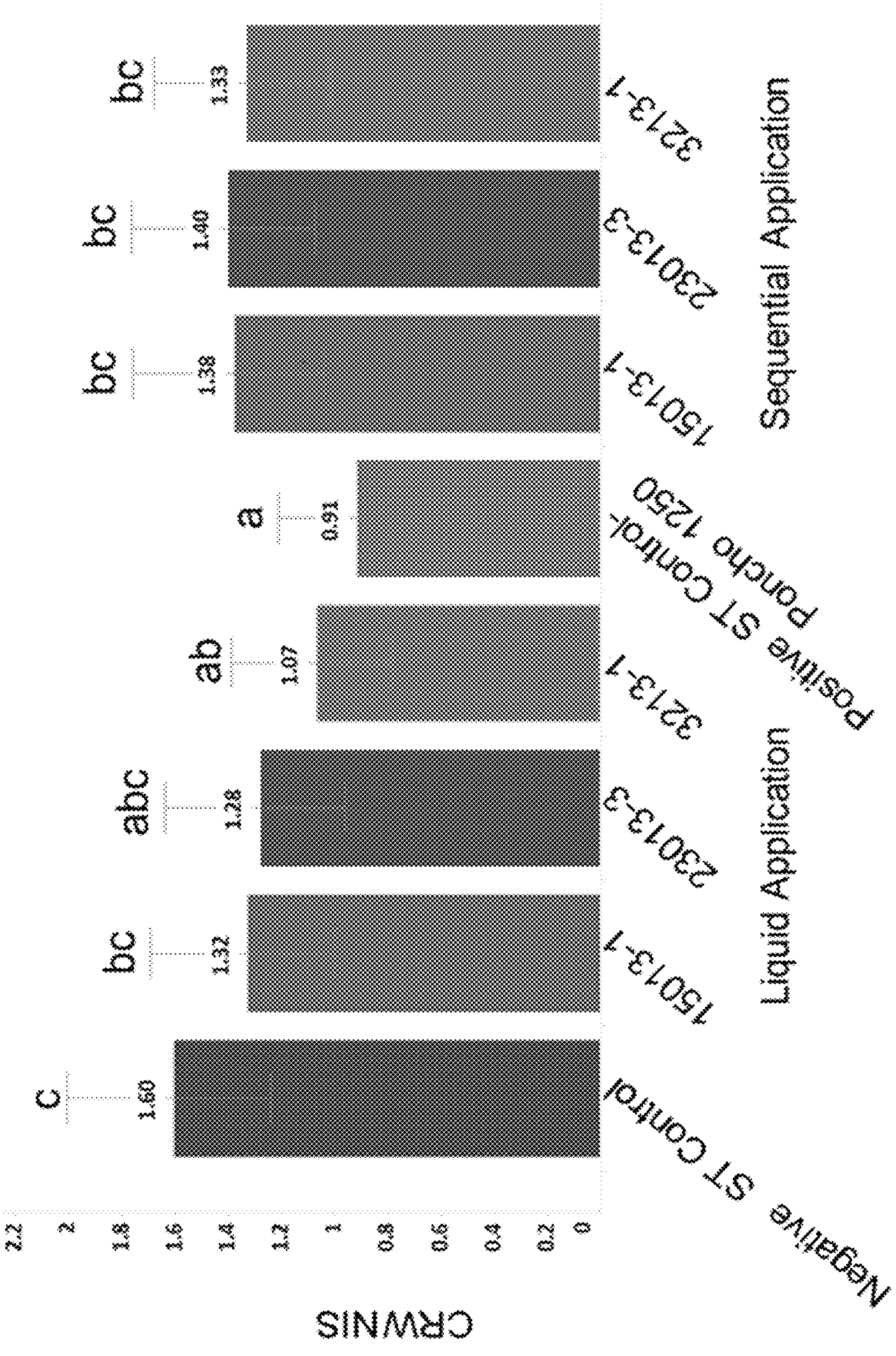
CRWNIS
0
0.2
0.4
0.6
0.8
1
1.2
1.4
1.6
1.8
2
2.2
c
1.60
bc
1.32
abc
1.28
ab
1.07
a
0.91
bc
1.38
bc
1.40
bc
1.33
Negative ST Control
15013-1
23013-3
3213-1
Positive ST Control-Poncho 1250
15013-1
23013-3
3213-1
Liquid Application
Sequential Application

BIOLOGICALS AND THEIR USE IN PLANTS

CROSS-REFERENCE TO RELATED APPLICATIONS

This application claims priority to U.S. Provisional Application No. 62/240,138, filed Oct. 12, 2015, which is hereby incorporated herein in its entirety by reference.

FIELD

Entomopathogenic fungal strains, entomopathogenic fungal compositions, and methods of using the strains and compositions for reducing overall insect damage.

BACKGROUND

There has been a long felt need for environmentally friendly compositions and methods for controlling or eradicating insect pests of agricultural significance, i.e., methods that are selective, environmentally inert, non-persistent, and biodegradable, and that fit well into insect pest management schemes.

SUMMARY

One embodiment of the invention relates to a composition comprising an entomopathogenic fungal strain selected from *Metarhizium robertsii* and *Metarhizium anisopliae*. In certain embodiments, the fungal entomopathogen comprises a spore, a microsclerotia, or a conidia. In some embodiments, a fungal entomopathogen has insecticidal activity In one embodiment, the disclosure relates to a composition for increasing resistance to a plant pest, pathogen, or insect or for increasing plant health and/or yield comprising one or more entomopathogenic fungal strains selected from the group consisting of *Metarhizium robertsii* 15013-1 (NRRL 67073), *Metarhizium robertsii* 23013-3 (NRRL 67075), *Metarhizium anisopliae* 3213-1 (NRRL 67074), or any combinations thereof. In another embodiment, the disclosure relates to a composition comprising an agriculturally accepted carrier and a fungal entomopathogen selected from the group consisting of *Metarhizium robertsii* 15013-1, *Metarhizium robertsii* 23013-3, *Metarhizium anisopliae* 3213-1, or any combinations thereof. In a further embodiment, the fungal entomopathogen comprises a spore, conidia, or microsclerotia. In another embodiment, the disclosure relates to a composition comprising one or more entomopathogenic fungal strains selected from the group consisting of *Metarhizium robertsii* 15013-1 (NRRL 67073), *Metarhizium robertsii* 23013-3 (NRRL 67075), *Metarhizium anisopliae* 3213-1 (NRRL 67074), mutants of these strains, a metabolite or combination of metabolites produced by a strain disclosed herein that exhibits insecticidal activity towards a plant pest, pathogen or insect, or any combinations thereof.

In yet another embodiment, the disclosure relates to a composition comprising at least two entomopathogenic fungal strains selected from the group consisting of *Metarhizium robertsii* 15013-1, *Metarhizium robertsii* 23013-3, *Metarhizium anisopliae* 3213-1, or any combination thereof, in an effective amount to achieve an effect of inhibited growth of a plant pathogen, pest or insect. In another embodiment, a composition disclosed herein further comprises a biocontrol agent selected from the group consisting of bacteria, fungi, yeast, protozoans, viruses, entomopathogenic nematodes, botanical extracts, proteins, secondary metabolites, and inoculants.

In another embodiment, a composition comprises a fungal entomopathogen and one or more agrochemically active compounds selected from the group consisting of: an insecticide, a fungicide, a bactericide, and a nematicide. In one embodiment, the fungicide comprises a fungicide composition selected from the group consisting of azoxystrobin, thiabendazole, fludioxonil, metalaxyl, tebuconazole, prothioconazole, ipconazole, penflufen, and sedaxane. In another embodiment, a composition comprises a fungal entomopathogen, wherein the fungal entomopathogen is resistant to a fungicide. In another embodiment, a composition comprises a fungal entomopathogen, wherein the fungal entomopathogen retains insecticidal activity in the presence of a fungicide. In still another embodiment, the composition further comprises a compound selected from the group consisting of a safener, a lipo-chitooligosaccharide, an isoflavone, and a ryanodine receptor modulator.

In another embodiment, a composition disclosed herein further comprises at least one at least one seed, plant or plant part. In one embodiment, the seed, plant, or plant part is genetically modified or a transgenic seed, plant or plant part. In a further embodiment, the genetically modified or transgenic seed, plant, or plant part comprises an insecticidal trait derived from a plant, a bacteria, a non-Bt bacteria, an archea, an insect, or animal. In some embodiments, the insecticidal trait comprises a *Coleopteran* insecticidal trait. In some embodiments, an insecticidal trait may include a Bt trait, a non-Bt trait, and/or an RNAi trait. In some embodiments, the compositions disclosed herein are applied as a seed coating, an in-furrow application, or as a foliar application.

In one embodiment, a composition disclosed controls one or more plant pathogens, pests, or insects or inhibits the growth of one or more plant pathogens, pest or insects including, but not limited to, a bacteria, a fungus, a virus, a protozoa, nematode or an arthropod. In one embodiment, a composition disclosed herein controls or inhibits the growth of an insect, including, but not limited to a *Coleopteran, Hemipteran*, or *Lepidopteran* insect. In still another embodiment, a composition disclosed herein controls or inhibits the growth of *Diabrotica virgifera virgifera.*

In another embodiment, a composition disclosed herein is an effective amount to provide pesticidal activity to bacteria, plants, plant cells, tissues and seeds. In another embodiment, the composition is an effective amount to provide pesticidal activity to *Coleopteran* or *Lepidopteran* insects. In still another embodiment, the composition is an effective amount to provide pesticidal activity to *Diabrotica virgifera virgifera.*

In another embodiment, a composition disclosed herein is in an effective amount to improve plant performance including but not limited to increased root formation, increased root mass, increased root function, increased shoot height, increased shoot function, increased flower bud presence, increased flower bud formation, increased seed germination, increased yield, increased total plant wet weight, and increased total plant dry weight.

In another embodiment, the disclosure relates to a method comprising applying a composition comprising one or more entomopathogenic fungal strains selected from the group consisting of *Metarhizium robertsii* 15013-1, *Metarhizium robertsii* 23013-3, *Metarhizium anisopliae* 3213-1, or any combination thereof.

In another embodiment, the disclosure relates to a method comprising applying a composition comprising one or more entomopathogenic fungal strains selected from the group consisting of *Metarhizium robertsii* 15013-1, *Metarhizium robertsii* 23013-3, *Metarhizium anisopliae* 3213-1, or any combination thereof to a seed, a plant, plant part or soil in an effective amount to achieve an effect selected from the group consisting of: inhibit a plant pathogen, pest, or insect or to prevent damage to a plant by a pathogen, pest, or insect, improve plant performance, improve plant yield, improve plant vigor, increase phosphate availability, increase production of a plant hormone, increase root formation, increase shoot height in a plant, increase leaf length of a plant, increase flower bud formation of a plant, increase total plant fresh weight, increase total plant dry weight, and increase seed germination.

In yet another embodiment, the disclosure relates to a method comprising applying a composition comprising at least two entomopathogenic fungal strains selected from the group consisting of *Metarhizium robertsii* 15013-1, *Metarhizium robertsii* 23013-3, *Metarhizium anisopliae* 3213-1, or any combination thereof to a seed, a plant, plant part or soil in an effective amount to achieve an effect selected from the group consisting of: to inhibit a plant pathogen, pest, or insect, damage to a plant by a pathogen, pest, or insect, improve plant performance, improve plant yield, improve plant vigor, increase phosphate availability, increase production of a plant hormone, increase root formation, increase shoot height in a plant, increase leaf length of a plant, increase flower bud formation of a plant, increase total plant fresh weight, increase total plant dry weight, and increase seed germination.

In another embodiment, the methods disclosed herein further comprise applying a composition further comprising a biocontrol agent, wherein the biocontrol agent selected from the group consisting of bacteria, fungi, yeast, protozoans, viruses, entomopathogenic nematodes, botanical extracts, proteins, secondary metabolites, and inoculants.

In yet another embodiment, the methods disclosed herein further comprise applying a composition further comprising at least two strains are selected from the group consisting of: *Metarhizium robertsii* 15013-1, *Metarhizium robertsii* 23013-3, *Metarhizium anisopliae* 3213-1 and combinations thereof.

In yet another embodiment, the methods disclosed herein further comprise applying a composition comprising one or more agrochemically active compounds selected from the group consisting of: an insecticide, a fungicide, a bactericide, and a nematicide. In one embodiment, the fungicide comprises a fungicide composition selected from the group consisting of azoxystrobin, thiabendazole, fludioxonil, metalaxyl, tebuconazole, prothioconazole, ipconazole, penflufen, sedaxane. In another embodiment, a composition comprises a fungal entompathogen, wherein the fungal entomopathogen is resistant to a fungicide. In another embodiment, a composition comprises a fungal entompathogen, wherein the fungal entomopathogen retains insecticidal activity in the presence of a fungicide.

In still another embodiment, the methods disclosed herein further comprise applying a composition further comprising a compound selected from the group consisting of a safener, a lipo-chitooligosaccharide, an isoflavone, and a ryanodine receptor modulator.

In another embodiment, the methods disclosed herein further comprise applying the composition in an effective amount to inhibit growth of a plant pathogen, including but not limited to bacteria, a fungus, a nematode, an insect, a virus, and a protozoa.

In another embodiment, the methods disclosed herein further comprise applying the composition in an effective amount to provide pesticidal activity to bacteria, plants, plant cells, tissues and seeds. In another embodiment, the composition is an effective amount to provide pesticidal activity to *Coleopteran, Hemipteran* or *Lepidopteran* insects. In still another embodiment, the composition is an effective amount to provide pesticidal activity to *Diabrotica virgifera virgifera.*

In another embodiment, the methods disclosed herein relate to increasing durability of a *Coleopteran* insecticidal trait of a genetically modified or transgenic seed, plant part, or plant to a plant pathogen, a pest, or an insect comprising inoculating a genetically modified or transgenic seed, plant part, or plant with a composition comprising a fungal entomopathogen selected from the group consisting of *Metarhizium robertsii* 15013-1, *Metarhizium robertsii* 23013-3, and *Metarhizium anisopliae* 3213-1, wherein the genetically modified or transgenic seed, plant part or plant comprises a *Coleopteran* insecticidal trait.

DESCRIPTION OF THE DRAWINGS

FIG. 1. Field study CRWNIS results of liquid or sequential application of 15013-1, 23013-3, and 3213-1 strain formulations under insect pressure.

DETAILED DESCRIPTION

The embodiments of the invention are not limited by the exemplary methods and materials disclosed, and any methods and materials similar or equivalent to those described can be used in the practice or testing of embodiments of this invention. Numeric ranges are inclusive of the numbers defining the range.

The headings provided are not limitations of the various aspects or embodiments of this invention, which can be had by reference to the specification.

Other definitions of terms may appear throughout the specification. It is to be understood the embodiments of the invention are not limited to particular embodiments described, and additional embodiments may vary. It is also to be understood that the terminology used is to describe the embodiments only, and is not intended to be limiting, since the scope of the embodiments of the invention will be limited only by the appended claims and equivalents thereof.

The article “a” and “an” are used to refer to one or more than one (i.e., to at least one) of the grammatical object of the article. For example, “an element” means one or more element.

As used herein, “administer” refers to the action of introducing a strain and/or a composition to an environment for pathogen, pest, or insect inhibition or to improve plant performance.

As used herein, the term “agrochemically active compounds” refers to any substance that is or may be customarily used for treating plants including, but not limited to, fungicides, bactericides, insecticides, acaricides, nematicides, molluscicides, safeners, plant growth regulators, and plant nutrients, as well as, microorganisms. Compositions disclosed herein may comprise fungicides which may include, but are not limited to, the respiration inhibitors, such as azoxystrobin, which target complex III of mitochondrial electron transport; tubulin inhibitors, such as thiabendazole, which bind to beta-tubulin; the osmotic stress related-kinase inhibitor fludioxonil; an RNA polymerase inhibitor of Oomycetes, a group of fungal-like organisms, such as metalaxyl; inhibitors of sterol biosynthesis, which include inhibitors of the C-14 demethylase of the sterol biosynthesis pathway (commonly referred to as demethylase inhibitors or Mils), such as tebuconazole, prothioconazole, and ipconazole; a respiration inhibitor which targets complex II mitochondrial electron transport, such as a penflufen; a respiration inhibitor which targets complex II mitochondrial electron transport, such as sedaxane. Other classes of fungicides with different or similar modes of action can be found at frac.infoldocs/default-sourcelpublicationslirac-code-listlfrac-code-list-2016.pdf?sfvrsn=2 (which can be accessed on the world-wide web using the "www" prefix; See Hirooka and Ishii (2013), *Journal of General Plant Pathology*). A fungicide may comprise all or any combination of different classes of fungicides as described herein. In certain embodiments, a composition disclosed herein comprises azoxystrobin, thiabendazole, fludioxonil, and metalaxyl. In another embodiment, a composition disclosed herein comprises a tebuconazole. In another embodiment, a composition disclosed herein comprises prothioconazole, metalaxyl, and penflufen. In another embodiment, a composition disclosed herein comprises ipconazole and metalaxyl. In another embodiment, a composition disclosed herein comprises sedaxane. As used herein, a composition may be a liquid, a heterogeneous mixture, a homogeneous mixture, a powder, a solution, a dispersion or any combination thereof.

As used herein, "effective amount" refers to a quantity of entomopathogenic fungal strain or entomopathogenic fungal composition sufficient to inhibit growth of a pathogenic microorganism or to impede the rate of growth of the pathogenic microorganism. In another embodiment, the term "effective amount" refers to a quantity of entomopathogenic fungal strain or entomopathogenic fungal composition sufficient to improve plant performance. In another embodiment, the term "effective amount" refers to a quantity of entomopathogenic fungal strain or entomopathogenic fungal composition sufficient to control, kill, inhibit, and reduce the number, emergence, or growth of a pathogen, pest, or insect. In another embodiment, the term "effective amount" refers to a quantity of entomopathogenic fungal strain or entomopathogenic fungal composition sufficient to prevent damage from a pathogen, pest, or insect. One skilled in the art will recognized that an effective amount of entomopathogenic fungal strain or entomopathogenic fungal composition may not reduce the numbers of pathogens, pests or insects, but is effective in decreasing damage to plants and/or plant parts as a result of a pathogen, pest or insect. For example, a pesticidally effective amount may reduce pathogen, pest or insect emergence, or damage to seeds, roots, shoots, or foliage of plants that are treated compared to those that are untreated.

As used herein, the term "entomopathogenic fungal strain" or "entomopathogenic fungal composition" includes, but is not limited to conidia spores, spores, mycelia, microsclerotia, and/or any other life cycle stage of a fungal entomopathogen.

As used herein, the term "inhibit" refers to destroy, reduce, resist, control, decrease, slow or otherwise interfere with the growth or survival of a pathogen, pest, or insect when compared to the growth or survival of the pathogen, pest, or insect in an untreated control. Any of the terms of inhibit, destroy, control, decrease, slow, interfere, resist, or reduce may be used interchangeably. In one embodiment, to "inhibit" is to destroy, control, reduce, resist, decrease, slow or otherwise interfere with the growth, emergence, or survival of a pathogen, pest, or insect by at least about 3% to at least about 100%, or any value in between for example at least about 10%, 15%, 20%, 25%, 30%, 35%, 40%, 45%, 50%, 55%, 60%, 65%, 70%, 75%, 80%, 85%, 90%, 95%, 99%, or 100% when compared to the growth or survival of the pathogen, pest, or insect in an untreated control. The amount of inhibition can be measured as described herein or by other methods known in the art. As used herein, "protects a plant from a pathogen, pest, or insect pest" is intended to mean the limiting or eliminating of the pathogen, pest, or insect related damage to a plant and/or plant part by, for example, inhibiting the ability of the pathogen, pest, or insect to grow, emerge, feed, and/or reproduce or by killing the pathogen, pest, or insect. As used herein, pesticidal and/or insecticidal activity refers to an activity of compound, composition, and or method that protects a plant and/or plant part from a pathogen, pest, or insect.

In an embodiment of the invention, inhibition a pathogen, pest, or insect lasts for or provides protection for greater than a day, two days, three days, four days, five days, six days, a week, two weeks, three weeks, a month or more after an entomopathogenic fungal strain or entomopathogenic fungal composition disclosed herein is applied to subject material. In another embodiment, inhibition a pathogen, pest or insect lasts from one to seven days, from seven to 14 days, from 14 to 21 days, or from 21 to 30 days or more. In another embodiment, the inhibition of the growth of a pathogen, pest, or insect lasts for or provides protection for greater than the time from application to adult emergence of the pathogen, pest, or insect.

As used herein, the term "genetically modified" is intended to mean any species containing a genetic trait, loci, or sequence that was not found in the species or strain prior to manipulation. A genetically modified plant may be transgenic, cis-genic, genome edited, or bred to contain a new genetic trait, loci, or sequence. A genetically modified plant may be prepared by means known to those skilled in the art, such as transformation by bombardment, by a Cas/CRISPR or TALENS system, or by breeding techniques. As used herein, a "trait" is a new or modified locus or sequence of a genetically modified plant, including but not limited to a transgenic plant. A trait may provide herbicide or insect resistance to the genetically modified plant. As used herein, a "transgenic" plant, plant part, or seed refers to a plant, plant part, or seed containing at least one heterologous gene that allows the expression of a polynucleotide or polypeptide not naturally found in the plant.

As used herein, the term "environment of a plant or plant part" is intended to mean the area surrounding the plant or plant part, including but not limited to the soil, the air, or in-furrow. The environment of a plant or plant part may be in close proximity, touching, adjacent to, or in the same field as the plant or plant part. The compositions described herein may be applied to the environment of the plant or plant part as a seed treatment, as a foliar application, as a granular application, as a soil application, or as an encapsulated application. As used herein, "in-furrow" is intended to mean within or near the area where a seed is planted. The compositions disclosed herein may be applied in-furrow concurrently or simultaneously with a seed. In another embodiment, the compositions disclosed herein may be applied sequentially, either before or after a seed is planted.

As used herein, the term "different mode of action" is used to refer to a pesticidal composition controlling a pathogen, pest, or insect through a pathway or receptor that is different from another pesticidal composition. As used herein, the term "different mode of action" includes the pesticidal effects of one or more pesticidal compositions to different binding sites (i.e., different toxin receptors and/or different sites on the same toxin receptor) in the gut membranes of insects or through the RNA interference pathway to different target genes.

As used herein, the teen "pathogen, pest, or insect" includes but is not limited to pathogenic fungi, bacteria, mites, ticks, pathogenic microorganisms, and nematodes, as well as insect from the orders Coleoptera, Lepidoptera, Mallophaga, Homoptera, Hemiptera, Orihroptera, Thysanoptera, Dermaptera, Isoptera, Anoplura, Siphomatpera, Trichoptera, and others, including but not limited to *Diabrotica virgifera virgifera, Diabrotica undecimpunctata howardi, Diabrotica speciosa*, and *Diabrotica barberi.*

Embodiments of the present invention are useful in the inhibition of larvae and adults of the order Coleoptera from the families Anthribidae, Bruchidae and Curculionidae (including, but not limited to: *Anthonomus grandis* Boheman (boll weevil); *Lissorhoptrus oryzophilus* Kuschel (rice water weevil); *Sitophilus granarius* Linnaeus (granary weevil); *S. oryzae* Linnaeus (rice weevil); *Hypera punctata* Fabricius (clover leaf weevil); *Cylindrocopturus adspersus* LeConte (sunflower stem weevil); *Smicronyx fulvus* LeConte (red sunflower seed weevil); *S. sordidus* LeConte (gray sunflower seed weevil); *Sphenophorus maidis* Chittenden (maize billbug)); flea beetles, cucumber beetles, rootworms, leaf beetles, potato beetles and leafminers in the family Chrysomelidae (including, but not limited to: *Leptinotarsa decemlineata* Say (Colorado potato beetle); *Diabrotica virgifera virgifera* LeConte (western corn rootworm); *D. barberi* Smith and Lawrence (northern corn rootworm); *D. undecimpunctata howardi* Barber (southern corn rootworm); *Chaetocnema pulicaria* Melsheimer (corn flea beetle); *Phyllotreta cruciferae* Goeze (Crucifer flea beetle); *Phyllotreta striolata* (stripped flea beetle); *Colaspis brunnea* Fabricius (grape *colaspis*); *Oulema melanopus* Linnaeus (cereal leaf beetle); *Zygogramma exclamationis* Fabricius (sunflower beetle)); beetles from the family Coccinellidae (including, but not limited to: *Epilachna varivestis* Mulsant (Mexican bean beetle)); chafers and other beetles from the family Scarabaeidae (including, but not limited to: *Popillia japonica* Newman (Japanese beetle); *Cyclocephala borealis* Arrow (northern masked chafer, white grub); *C. immaculata* Olivier (southern masked chafer, white grub); *Rhizotrogus majalis* Razoumowsky (European chafer); *Phyllophaga crinita* Burmeister (white grub); *Ligyrus gibbosus* De Geer (carrot beetle)); carpet beetles from the family Dermestidae; wireworms from the family Elateridae, *Eleodes* spp., *Melanotus* spp.; *Conoderus* spp.; *Limonius* spp.; *Agriotes* spp.; *Ctenicera* spp.; *Aeolus* spp.; bark beetles from the family Scolytidae and beetles from the family Tenebrionidae.

Methods for measuring pesticidal activity are well known in the art. See, for example, Czapla and Lang, (1990) *J. Econ. Entomol.* 83:2480-2485; Andrews, et al., (1988) *Biochem. J.* 252:199-206; Marrone, et al., (1985) *J. of Economic Entomology* 78:290-293 and U.S. Pat. No. 5,743,477, all of which are herein incorporated by reference in their entirety. Generally, the pesticide is mixed and used in feeding assays. See, for example Marrone, et al., (1985) *J. of Economic Entomology* 78:290-293. Such assays can include contacting plants with one or more pests and determining the plant's ability to survive and/or cause the death of the pests.

As used herein, the term "plant" refers to all plants, plant parts, and plant populations, such as desirable and undesirable wild plants, cultivars, transgenic plants, and plant varieties (whether or not protectable by plant variety or plant breeder's rights). Cultivars and plant varieties can be plants obtained by conventional propagation and breeding methods that can be assisted or supplemented by one or more biotechnological methods such as by use of double haploids, protoplast fusion, random and directed mutagenesis, molecular or genetic markers or by bioengineering and genetic engineering methods.

The embodiments of the invention may generally be used for any plant species, including, but not limited to, monocots and dicots. Examples of plants of interest include, but are not limited to, corn (*Zea mays*), *Brassica* sp. (e.g., *B. napus, B. raga, B. juncea*), particularly those *Brassica* species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), *papaya* (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats, barley, vegetables ornamentals, and conifers.

As used herein, the term "plant parts" refers to all above ground and below ground parts and organs of plants such as shoot, leaf, blossom and root, whereby for example leaves, needles, stems, branches, blossoms, fruiting bodies, fruits and seeds, as well as roots, tubers, corms and rhizomes are included. Crops and vegetative and generative propagating material, for example, cuttings, corms, rhizomes, tubers, runners and seeds are also plant parts.

As used herein, the term "spore" includes, but is not limited to conidia spores, spores, mycelia, microsclerotia, and/or any other life cycle stage of a fungal entomopathogen. An "aerial conidiospore" (AC) refers to conidiospores formed by the asexual developmental cycle on the surface of an agar medium, or other solid substrate of appropriate composition. As used herein, term "submerged spores" refers to submerged conic pores and/or blastospores that develop in liquid culture.

As used herein, the term "viable" refers to a microbial cell, propagule, or spore that is metabolically active or able to differentiate. Thus, propagules, such as spores, are "viable" when they are dormant and capable of germinating.

Biological control of insect pests of agricultural significance using a microbial agent, such as fungi, bacteria, or another species of insect affords an environmentally friendly and commercially attractive alternative to synthetic chemical pesticides. Generally speaking, the use of biopesticides presents a lower risk of pollution and environmental hazards and biopesticides provide greater target specificity than is characteristic of traditional broad-spectrum chemical insecticides. In addition, biopesticides often cost less to produce and thus improve economic yield for a wide variety of crops.

Certain species of microorganisms of the genus *Bacillus* are known to possess pesticidal activity against a range of insect pests including *Lepidoptera, Diptera, Coleoptera, Hemiptera* and others. *Bacillus thuringiensis* (Bt) and *Bacillus popilliae* are among the most successful biocontrol agents discovered to date. Insect pathogenicity has also been attributed to strains of *B. larvae, B. lentimorbus, B. sphaericus* and *B. cereus*. Microbial insecticides, particularly those obtained from *Bacillus* strains, have played an important role in agriculture as alternatives to chemical pest control.

Crop plants have been developed with enhanced insect resistance by genetically engineering crop plants to produce pesticidal proteins from *Bacillus*. For example, corn and cotton plants have been genetically engineered to produce pesticidal proteins isolated and/or engineered from strains of Bt (herein referred to as a "Bt trait"). These genetically modified crops are now widely used in agriculture and have provided the farmer with an environmentally friendly alternative to traditional insect-control methods. While they have proven to be very successful commercially, these genetically modified, insect-resistant crop plants provide resistance to only a narrow range of the economically important insect pests. In some cases, insects can develop resistance to different insecticidal compounds, which raises the need to identify alternative biological control agents for pest control.

The embodiments of the invention relate to entomopathogenic fungal strains, entomopathogenic fungal compositions and methods of using the strains and compositions. In one embodiment the entomopathogenic strains have insecticidal activity and may find use in inhibiting, controlling, or killing a pathogen, pest, or insect, including, but is not limited to, fungi, pathogenic fungi, bacteria, mites, ticks, pathogenic microorganisms, and nematodes, as well as insects from the orders Coleoptera, Diptera, Hymenoptera, Lepidoptera, Mallophaga, Homoptera, Hemiptera Orthroptera, Thysanoptera, Dermaptera, Isoptera, Anoplura, Siphonaptera, Trichoptera, etc., particularly Coleoptera, including but not limited to *Diabrotica virgifera virgifera, Diabrotica undecimpunctata howardi*, and *Diabrotica barberi*, and for producing compositions with pesticidal activity.

In one embodiment, the entomopathogenic fungal strain(s) are selected from the group consisting of: *Metarhizium robertsii* 15013-1*, Metarhizium robertsii* 23013-3*, Metarhizium anisopliae* 3213-1, and combinations thereof.

*Metarhizium robertsii* 15013-1 (NRRL 67073) was deposited on Jun. 18, 2015 at the Agricultural Research Service Culture Collection (NRRL), 1815 North University Street, Peoria, Ill., 61604 and given accession number NRRL 67073. The deposits were made under the provisions of the Budapest Treaty on the International Recognition of the Deposit of Microorganisms for the Purposes of Patent Procedure.

*Metarhizium robertsii* 23013-3 (NRRL 67075) was deposited on Jun. 18, 2015 at the Agricultural Research Service Culture Collection (NRRL), 1815 North University Street, Peoria, Ill., 61604 and given accession number NRRL 67075. The deposits were made under the provisions of the Budapest Treaty on the International Recognition of the Deposit of Microorganisms for the Purposes of Patent Procedure.

*Metarhizium anisopliae* 3213-1 (NRRL 67074) was deposited on Jun. 18, 2015 at the Agricultural Research Service Culture Collection (NRRL), 1815 North University Street, Peoria, Ill., 61604 and given accession number NRRL 67074. The deposits were made under the provisions of the Budapest Treaty on the International Recognition of the Deposit of Microorganisms for the Purposes of Patent Procedure.

In an embodiment, a method of producing a fungal entomopathogen product in a liquid fermentation is disclosed. In an embodiment, a method consists of first generating aerial conidiospores of a fungal entomopathogen on an agar media, and then inoculating the aerial conidiospores into a liquid medium to generate a fungal entomopathogen product. In another embodiment, a method consists of first generating aerial conidiospores of a fungal entomopathogen on a solid substrate, including, but not limited to, an agar media or other solid media of appropriate composition, followed by inoculating the aerial conidiospores into a liquid medium to generate a fungal entomopathogen seed culture, followed by inoculating the fungal entomopathogen seed culture into a liquid medium to generate a fungal entomopathogen product. In another embodiment, a first fungal entomopathogen seed culture may be used to generate a second fungal entomopathogen seed culture, wherein the second seed culture is used to inoculate into a liquid medium to generate a fungal entomopathogen product. A liquid medium used to produce a fungal entomopathogen product may contain minerals, vitamins, a carbon source and a complex nitrogen source. In another embodiment, a nitrogen source is a complex source that comprises carbon, but is not a carbon source. In an embodiment, a method to produce a fungal entomopathogen product comprising a spore, a vegetative mycelium, a submerged spore, and/or a microsclerotia is disclosed. In an embodiment, a composition comprises a fermentation product of a fungal entomopathogen from a liquid fermentation. A fermentation product may be vacuum dried, spray dried, or fluidized bed dried for use to control plant pathogens, pests, or insects. In an embodiment, a method of producing a fungal entomopathogen product in a liquid fermentation, wherein the liquid fermentation comprises a liquid medium comprising minerals, vitamins, a carbon source, and a nitrogen source is disclosed. In an embodiment, a method of producing a fungal entomopathogen in a liquid culture using a carbon source and a nitrogen source is disclosed. In another embodiment, a method of producing a fungal entomopathogen in a liquid culture using two carbon sources and a nitrogen source is disclosed. In another embodiment, a method of producing a fungal entomopathogen in a liquid culture using two or more carbon sources and a nitrogen source is disclosed. In an embodiment, a carbon source is glucose. In another embodiment, a carbon source comprises a fructose, a galactose, a sorbitol, a sorbose, a sucrose, an arabinose, a maltodextrin, a ribose, or a xylose molecule and combinations thereof. In another embodiment, a first carbon source is in a limiting concentration. In a further embodiment, a second carbon source creates a non-optimal or stress condition that changes a physiological state of a fungal entomopathogen. In another embodiment, a method of producing a fungal entomopathogen in a liquid culture using a carbon source, a first nitrogen source, and a second nitrogen source, wherein the first nitrogen source is in a limiting concentration is disclosed.

In another embodiment, a method of producing a fungal entomopathogen in a liquid culture using a carbon source and a nitrogen source and controlling a fermentation parameter, wherein controlling the fermentation parameter creates a non-optimal or stress condition that changes a physiological state of a fungal entomopathogen is disclosed. In an embodiment a fermentation parameter may include a pH level, a carbon dioxide evolution rate, a dissolved oxygen percentage, an agitation profile, a sugar feed rate, or any other measured parameter of a fermentation of a fungal entomopathogen that may create a non-optimal or stress condition resulting in a change of a physiological state of a fungal entomopathogen. Physiological changes (switch to asexual cycle) may occur as a result of imposing stress or non-optimal conditions on a fungal entomopathogen. (See Steyaert et al. (2010), *Microbiol.* and Gao et al. (2007) *Mycol. Res*). In another embodiment, a method of producing a fungal entomopathogen in a liquid culture using at least two carbon sources and a nitrogen source and controlling a fermentation parameter, wherein controlling the fermentation parameter creates a non-optimal or stress condition that results in a change of a physiological state of a fungal entomopathogen is disclosed. In an embodiment, obtaining aerial conidiospores of a fungal entomopathogen comprises first generating aerial conidiospores of the fungal entomopathogen on an agar media or a solid state media (Dorta and Arcas (1998), *Enzyme Microb. Technol.*).

In an embodiment, a method for producing a fungal entomopathogenic product comprises generation of aerial conidiospores (AC) used as an inoculum for liquid cultures or liquid fermentations. Such methods include, but are not limited to, generation of ACs by inoculating a fungal entomopathogen strain on large potato destrose agar (PDA) or VM plates and incubating at 28° C. for about 2 to 3 weeks; flooding the plates with a solution of 0.05% Tween 80; and suspending ACs in the solution by gently scraping the surface of the plate culture. In an embodiment, an AC suspension may be filtered, and the ACs pooled to a high concentration. In a further embodiment, an AC concentration may be determined using a hemocytometer, the ACs centrifuged, and the AC pellet re-suspended using a solution of 15% glycerol in 0.05% Tween 80. In another embodiment, aerial conidiospores may also be obtained by solid state fermentation (Dorta and Arcas (1998), *Enzyme Microb. Technol.*).

In an embodiment, producing a fungal entomopathogen product in a liquid culture may comprise media volumes of 50 mL at shake flask fermentation scale, 1 L at 2 L benchtop fermentation scale, and 10 L at bioreactor fermentation scale, or up to 600,000 L fermentation scale. Media for seed or production cultures may comprise components as shown in Tables 1, 2 and 3. At shake flask scale media may be inoculated directly with aerial conidiospores (AC) at a final concentration of about $5\times10^6$ AC/mL. At benchtop or bioreactor scale media may be inoculated using a seed culture of about 40 mL or 400 mL of seed culture, respectively. A seed culture may be produced to build up biomass for a production culture. Seed cultures may be generated by further incubating a culture from about 1 to 7 days at about 28° C., and agitating from about 100 to 300 rpm. Upon addition of an inoculum, production cultures may be incubated from about 4 to 7 days at about 16° C. to 32° C. in an orbital shaker at about 300 rpm at shake flask scale; about 500 to 1200 rpm agitation at benchtop scale; or with agitation speeds equivalent to the benchtop impeller tip speed at bioreactor scale. In certain embodiments, water may be added to reduce the viscosity of a broth during fermentation. Pressure in a fermentation tank may be set at about 0.5 to 1 barg. In certain embodiments, a 50% (w/w) fructose solution may be fed after an initial glucose and fructose solution is exhausted. In certain embodiments, a seed or a production culture may have no pH control, one-sided (base addition only) pH control, or two-sided (base and acid addition) pH control. During a fermentation and/or at the end of a fermentation a variety of parameters may be recorded, such as, but not limited to, microsclerotia (MS) production, submerged spore (SS) production, biomass build-up expressed through grams of dry cell weight per kilogram of broth (DCW), carbon evolution rate (CER), oxygen uptake rate (OUR), dissolved oxygen (DO), ammonia concentration, pH, feed rate, carbon source content, and agitation.

TABLE 1

Vitamins present in all media.

| Vitamins | Final concentration [mg/L] |
|---|---|
| Thiamine•HCl (Vit. B1) | 0.5 |
| Riboflavin (Vit. B2) | 0.5 |
| Calcium Pantonthenate (Vit. B5) | 0.5 |
| Nicotinic Acid (Vit. B3) | 0.5 |
| Pyridoxamine | 0.5 |
| Thioctic Acid (Lipoic Acid) | 0.5 |
| Folic Acid (Vit. B9) | 0.05 |
| D-Biotin (Vit. B7) | 0.05 |
| Cobalamin (Vit. B12) | 0.05 |

TABLE 2

Basal salts present in all media.

| Basal salts | Final concentration [amount/L] |
|---|---|
| $KH_2PO_4$ | 4 g |
| $CaCl_2$•$2H_2O$ | 0.8 g |
| $MgSO_4$•$7H_2O$ | 0.6 g |
| 0.1M $CoCl_2$ | 1.555 mL |
| 10 g/L $MnSO_4$•$H_2O$ | 1.6 mL |
| 10 g/L $ZnSO_4$•$7H_2O$ | 1.4 mL |

TABLE 3

Carbon and nitrogen sources in different liquid media.

| | Carbon and nitrogen source concentrations in different media | | | | | | | | | |
|---|---|---|---|---|---|---|---|---|---|---|
| | Soy 10C:1N | Soy 10C:1N 25% Glu75% Fru | Soy 10C:1N 25% Glu75% Gal | Soy 10C:1N 25% Glu75% Sorbitol | Soy 10C:1N 25% Glu75% Sorbose | Soy 10C:1N 25% Glu75% Suc | Soy 10C:1N 25% Glu75% Ara | Soy 10C:1N 25% Glu75% Mal | Soy 10C:1N 25% Glu75% Rib | Soy 10C:1N 25% Glu75% Xyl |
| Soy flour | 45 g | 45 g | 45 g | 45 g | 45 g | 45 g | 45 g | 45 g | 45 g | 45 g |
| D-Glucose | 49.5 g | 12.375 g | 12.375 g | 12.375 g | 12.375 g | 12.375 g | 12.375 g | 12.375 g | 12.375 g | 12.375 g |
| D-Fructose | | 37.125 g | | | | | | | | |
| D-Galactose | | | 37.125 g | | | | | | | |
| D-Sorbitol | | | | 37.125 g | | | | | | |
| L-Sorbose | | | | | 37.125 g | | | | | |
| Sucrose | | | | | | 37.125 g | | | | |
| L-Arabinose | | | | | | | 37.125 g | | | |
| Maltodextrin | | | | | | | | 37.125 g | | |

TABLE 3-continued

| Carbon and nitrogen sources in different liquid media. | | | | | | | | | | |
|---|---|---|---|---|---|---|---|---|---|---|
| | Carbon and nitrogen source concentrations in different media | | | | | | | | | |
| | Soy 10C:1N | Soy 10C:1N 25% Glu75% Fru | Soy 10C:1N 25% Glu75% Gal | Soy 10C:1N 25% Glu75% Sorbitol | Soy 10C:1N 25% Glu75% Sorbose | Soy 10C:1N 25% Glu75% Suc | Soy 10C:1N 25% Glu75% Ara | Soy 10C:1N 25% Glu75% Mal | Soy 10C:1N 25% Glu75% Rib | Soy 10C:1N 25% Glu75% Xyl |
| D-ribose | | | | | | | | | 37.125 g | |
| D-xylose | | | | | | | | | | 37.125 g |

*In some cases, soy flour was substituted with other sources of nitrogen, such as, but not limited to cottonseed flour, yeast extract or Casamino acids; in some cases the ratio of carbon (C) to nitrogen (N) was 30:1, or 50:1.

In certain embodiments, recovering and formulating a fungal entomopathogen (*Metarhizium* spp.) product from a liquid culture comprises cooling and harvesting a fermentation broth. A fermenter may be rinsed with about 1× to 2× the volume of a fermentation broth, and the diluted broth pooled with the neat broth. A diluted entomopathogenic fungal material in a fermentation broth may be treated with DE Admix. A treated fermentation broth may be filtered through a Büchner filter. A filter cake may be processed immediately, or stored in a cold room until processing. A wet filter cake may be broken up and dried in a vacuum drier for about 48 h to 5 days. A dried filter cake may be ground to create a final entomopathogenic fungal dried powder product.

One embodiment relates to a composition comprising or consisting of or consisting essentially of an entomopathogenic fungal strain selected from the group consisting of: *Metarhizium robertsii* 15013-1, *Metarhizium robertsii* 23013-3, and *Metarhizium anisopliae* 3213-1. In another embodiment, the composition comprises, consists of, or consists essentially of at least two or more entomopathogenic fungal strains selected from the group consisting of: *Metarhizium robertsii* 15013-1, *Metarhizium robertsii* 23013-3, *Metarhizium anisopliae* 3213-1. In a further embodiment, the composition comprises, consists of, or consists essentially of the entomopathogenic fungal strains selected from the group consisting of: *Metarhizium robertsii* 15013-1, *Metarhizium robertsii* 23013-3, and *Metarhizium anisopliae* 3213-1. In an embodiment, a composition is a biologically pure culture of *Metarhizium robertsii* 15013-1, *Metarhizium robertsii* 23013-3, and *Metarhizium anisopliae* 3213-1 and combinations thereof.

One embodiment of the invention relates to a composition comprising the entomopathogenic fungal strains disclosed herein and one or more compounds or agents selected from the group consisting of: agrochemically active compounds, biocontrol agents, lipo-chitooligosaccharide compounds (LCDs), isoflavones, quinazolines, insecticidal compounds, azolopyrimidinylamines, polymeric compounds, ionic compound, substituted thiophenes, substituted dithiines, fluopyramm, enaminocarbonyl compounds, strigolactone compound, and dithiino-tetracarboximide compounds and combinations thereof.

A further embodiment relates to the use of a first composition comprising the entomopathogenic fungal strains disclosed herein and a second composition comprising one or more compounds or agents selected from the group consisting of: agrochemically active compounds, biocontrol agents, lipo-chitooligosaccharide compounds (LCDs), isoflavones, quinazolines, insecticidal compound, azolopyrimidinylamine, polymeric compounds, ionic compound, substituted thiophenes, substituted dithiines, fluopyramm, enaminocarbonyl compounds, strigolactone compound, and dithiino-tetracarboximide compounds and combinations thereof.

In one embodiment, the disclosure relates to a composition comprising one or more entomopathogenic fungal strains disclosed herein and one or more biocontrol agents. As used herein, the term "biocontrol agent" ("BCA") includes bacteria, fungi or yeasts, protozoans, viruses, entomopathogenic nematodes, and botanical extracts, or products produced by microorganisms including proteins or secondary metabolite, and inoculants that have one or both of the following characteristics: (I) inhibits or reduces plant infestation and/or growth of pathogens, pests, or insects, including but not limited to pathogenic fungi, bacteria, and nematodes, as well as arthropod pests such as insects, arachnids, chilopods, diplopods, or that inhibits plant infestation and/or growth of a combination of plant pathogens, pests, or insects; (2) improves plant performance; (3) improves plant yield; (4) improves plant vigor; and (5) improves plant health.

In one embodiment, the disclosure relates to a composition comprising an entomopathogenic fungal strain disclosed herein and an agrochemically active compound. Agrochemically active compounds are substances that are or may be used for treating or applying to a seed, a plant, plant part, or the environment of the seed or plant or plant part including but not limited to fungicides, bactericides, insecticides, acaricides, nematicides, mothiscicides, safeners, plant growth regulators, plant nutrients, chemical entities with a known mechanism of action, additional microorganisms, and biocontrol agents.

In one embodiment, a composition disclosed herein comprises one or more agrochemically active compounds, wherein one compound is chlorantraniliprole) (Rynaxypyr®). In another embodiment, the composition comprises one or more agrochemically active compounds, wherein one compound is cyantraniliprole (Cyazypyr®). In another embodiment, the composition comprises both chlorantraniliprole and cyantraniliprole.

In an embodiment, a first and a second composition disclosed herein can be applied at the same time to a seed. In another embodiment, a first composition can be applied to a seed followed by application of a second composition to the seed. In yet another embodiment, a second composition can be applied to a seed followed by application of a first composition to the seed. In another embodiment, a first composition can be applied to a seed followed by application of a second composition to a plant. In yet another embodiment, a second composition can be applied to a seed followed by application of a first composition to a plant. In another embodiment, a first composition can be applied to a seed followed by application of a second composition to a plant part. In yet another embodiment, a second composition can be applied to a seed followed by application of a first composition to a plant part. In another embodiment, a first composition can be applied to a seed followed by application of a second composition to the environment of the seed. In yet another embodiment, a second composition can be applied to a seed followed by application of a first composition to the environment of the seed. In another embodiment, a first composition can be applied to a seed followed by application of a second composition to the environment of a plant. In yet another embodiment, a second composition can be applied to a seed followed by application of a first composition to the environment of a plant. In another embodiment, a first composition can be applied to a seed followed by application of a second composition to the environment of a plant part. In yet another embodiment, a second composition can be applied to a seed followed by application of a first composition to the environment of a plant part.

In an embodiment, a first and a second composition disclosed herein can be applied at the same time to a plant. In another embodiment, a first composition can be applied to a plant followed by application of a second composition to the plant. In yet another embodiment, a second composition can be applied to a plant followed by application of a first composition to the plant. In another embodiment, a first composition can be applied to a plant followed by application of a second composition to a seed. In yet another embodiment, a second composition can be applied to a plant followed by application of a first composition to a seed. In another embodiment, a first composition can be applied to a plant followed by application of a second composition to a plant part. In yet another embodiment, a second composition can be applied to a plant followed by application of a first composition to a plant part. In another embodiment, a first composition can be applied to a plant followed by application of a second composition to the environment of a seed. In yet another embodiment, a second composition can be applied to a plant followed by application of a first composition to the environment of a seed. In another embodiment, a first composition can be applied to a plant followed by application of a second composition to the environment of the plant. In yet another embodiment, a second composition can be applied to a plant followed by application of a first composition to the environment of the plant. In another embodiment, a first composition can be applied to a plant followed by application of a second composition to the environment of a plant part. In yet another embodiment, a second composition can be applied to a plant followed by application of a first composition to the environment of a plant part.

In an embodiment, a first and a second composition disclosed herein can be applied at the same time to a plant part. In another embodiment, a first composition can be applied to a plant part followed by application of a second composition to the plant part. In yet another embodiment, a second composition can be applied to a plant part followed by application of a first composition to the plant part. In another embodiment, a first composition can be applied to a plant part followed by application of a second composition to a seed. In yet another embodiment, a second composition can be applied to a plant part followed by application of a first composition to a seed. In another embodiment, a first composition can be applied to a plant part followed by application of a second composition to a plant. In yet another embodiment, a second composition can be applied to a plant part followed by application of a first composition to a plant. In another embodiment, a first composition can be applied to a plant part followed by application of a second composition to the environment of a seed. In yet another embodiment, a second composition can be applied to a plant part followed by application of a first composition to the environment of a seed. In another embodiment, a first composition can be applied to a plant part followed by application of a second composition to the environment of a plant. In yet another embodiment, a second composition can be applied to a plant part followed by application of a first composition to the environment of a plant. In another embodiment, a first composition can be applied to a plant part followed by application of a second composition to the environment of the plant part. In yet another embodiment, a second composition can be applied to a plant part followed by application of a first composition to the environment of the plant part.

In an embodiment, a first and a second composition disclosed herein can be applied at the same time to the environment of a seed. In another embodiment, a first composition can be applied to the environment of a seed followed by application of a second composition to the environment of the seed. In yet another embodiment, a second composition can be applied to the environment of a seed followed by application of a first composition to the environment of the seed. In another embodiment, a first composition can be applied to the environment of a seed followed by application of a second composition to a seed. In yet another embodiment, a second composition can be applied to the environment of a seed followed by application of a first composition to a seed. In another embodiment, a first composition can be applied to the environment of a seed followed by application of a second composition to a plant. In yet another embodiment, a second composition can be applied to the environment of a seed followed by application of a first composition to a plant. In another embodiment, a first composition can be applied to the environment of a seed followed by application of a second composition to a plant part. In yet another embodiment, a second composition can be applied to the environment of a seed followed by application of a first composition to a plant part. In another embodiment, a first composition can be applied to the environment of a seed followed by application of a second composition to the environment of a plant. In yet another embodiment, a second composition can be applied to the environment of a seed followed by application of a first composition to the environment of a plant. In another embodiment, a first composition can be applied to the environment of a seed followed by application of a second composition to the environment of a plant part. In yet another embodiment, a second composition can be applied to the environment of a seed followed by application of a first composition to the environment of a plant part.

In an embodiment, a first and a second composition disclosed herein can be applied at the same time to the environment of a plant. In another embodiment, a first composition can be applied to the environment of a plant followed by application of a second composition to the environment of the plant. In yet another embodiment, a second composition can be applied to the environment of a plant followed by application of a first composition to the environment of the plant. In another embodiment, a first composition can be applied to the environment of a plant followed by application of a second composition to a seed. In yet another embodiment, a second composition can be applied to the environment of a plant followed by application of a first composition to a seed. In another embodiment, a first composition can be applied to the environment of a plant followed by application of a second composition to a plant. In yet another embodiment, a second composition can be applied to the environment of a plant followed by application of a first composition to a plant. In another embodiment, a first composition can be applied to the environment of a plant followed by application of a second composition to a plant part. In yet another embodiment, a second composition can be applied to the environment of a plant followed by application of a first composition to a plant part. In another embodiment, a first composition can be applied to the environment of a plant followed by application of a second composition to the environment of a seed. In yet another embodiment, a second composition can be applied to the environment of a plant followed by application of a first composition to the environment of a seed. In another embodiment, a first composition can be applied to the environment of a plant followed by application of a second composition to the environment of a plant part. In yet another embodiment, a second composition can be applied to the environment of a plant followed by application of a first composition to the environment of a plant part.

In an embodiment, a first and a second composition disclosed herein can be applied at the same time to the environment of a plant part. In another embodiment, a first composition can be applied to the environment of a plant part followed by application of a second composition to the environment of the plant part. In yet another embodiment, a second composition can be applied to the environment of a plant part followed by application of a first composition to the environment of the plant part. In another embodiment, a first composition can be applied to the environment of a plant part followed by application of a second composition to a seed. In yet another embodiment, a second composition can be applied to the environment of a plant part followed by application of a first composition to a seed. In another embodiment, a first composition can be applied to the environment of a plant part followed by application of a second composition to a plant. In yet another embodiment, a second composition can be applied to the environment of a plant part followed by application of a first composition to a plant. In another embodiment, a first composition can be applied to the environment of a plant part followed by application of a second composition to the environment of a seed. In yet another embodiment, a second composition can be applied to the environment of a plant part followed by application of a first composition the environment of a seed. In another embodiment, a first composition can be applied to the environment of a plant part followed by application of a second composition to the environment of a plant. In yet another embodiment, a second composition can be applied to the environment of a plant part followed by application of a first composition to the environment of a plant.

In one embodiment, the disclosure relates to the use of the entomopathological fungal strains disclosed herein with a composition comprising an insecticidal protein from *Pseudomonas* sp. such as PSEEN3174 (Monalysin; (2011) *PLoS Pathogens* 7:1-13); from *Pseudomonas protegens* strain CHA0 and Pf-5 (previously *fluorescens*) (Pechy-Tarr, (2008) *Environmental Microbiology* 10:2368-2386; GenBank Accession No. EU400157); from *Pseudomonas taiwanensis* (Liu, et al., (2010) *J. Agric. Food Chem.*, 58:12343-12349) and from *Pseudomonas pseudoalcligenes* (Zhang, et al., (2009) *Annals of Microbiology* 59:45-50 and Li, et al., (2007) *Plant Cell Tiss. Organ Cult.* 89:159-168); insecticidal proteins from *Photorhabdus* sp. and *Xenorhabdus* sp. (Hinchliffe, et al., (2010) *The Open Toxicology Journal*, 3:101-118 and Morgan, et al., (2001) *Applied and Envir. Micro.* 67:2062-2069); U.S. Pat. No. 6,048,838, and U.S. Pat. No. 6,379,946; a PIP-1 polypeptide of US Patent Publication US20140007292; an AfIP-1A and/or AfIP-1B polypeptide of US Patent Publication US20140033361; a PHI-4 polypeptide of U.S. Ser. No. 13/839,702; a PIP-47 polypeptide of PCT Serial Number PCT/US14/51063; a PIP-72 polypeptide of PCT Serial Number; a PtIP-50 polypeptide and a PtIP-65 polypeptide of PCT Publication Number WO2015/120270; a PtIP-83 polypeptide of PCT Publication Number WO2015/120276; a PtIP-96 polypeptide of PCT Serial Number PCT/US15/55502; PCT/US14/55128 and 6-endotoxins including, but not limited to, the Cry1, Cry2, Cry3, Cry4, Cry5, Cry6, Cry7, Cry8, Cry9, Cry10, Cry11, Cry12, Cry13, Cry14, Cry15, Cry16, Cry17, Cry18, Cry19, Cry20, Cry21, Cry22, Cry23, Cry24, Cry25, Cry26, Cry27, Cry 28, Cry 29, Cry 30, Cry31, Cry32, Cry33, Cry34, Cry35, Cry36, Cry37, Cry38, Cry39, Cry40, Cry41, Cry42, Cry43, Cry44, Cry45, Cry 46, Cry47, Cry49, Cry 51 and Cry55 classes of 6-endotoxin genes and the *B. thuringiensis* cytolytic Cyt1 and Cyt2 genes. Other Cry proteins are well known to one skilled in the art (see, Crickmore, et al., "*Bacillus thuringiensis* toxin nomenclature" (2011), at lifesci.sussex.ac.uk/home/Neil_Crickmore/Bt/which can be accessed on the world-wide web using the "www" prefix). The insecticidal activity of Cry proteins is well known to one skilled in the art (for review, see, van Frannkenhuyzen, (2009) *J. Invert. Path.* 101:1-16). The use of Cry proteins as transgenic plant traits is well known to one skilled in the art and Cry-transgenic plants including but not limited to Cry1Ac, Cry1Ac+Cry2Ab, Cry1Ab, Cry1A.105, Cry1F, Cry1Fa2, Cry1F+Cry1Ac, Cry2Ab, Cry3A, mCry3A, Cry3Bb1, Cry34Ab1, Cry35Ab1, Vip3A, mCry3A, Cry9c and CBI-Bt have received regulatory approval (see, Sanahuja, (2011) *Plant Biotech Journal* 9:283-300 and the CERA (2010) GM Crop Database Center for Environmental Risk Assessment (CERA), ILSI Research Foundation, Washington D.C. at cera-gmc.org/index.php?action=gm_crop_database which can be accessed on the world-wide web using the "www" prefix). As used herein, a "non-Bt trait" refers to any insecticidal gene or trait in a plant derived or modified from a naturally occurring bacterial, plant, or animal, excluding any *Bacillus* thurengiensis strain. Non-Bt traits include, but are not limited to a RNAi or dsRNA traits, a *Psuedomonas*-derived trait, or a plant-derived trait.

In one embodiment the disclosure relates to the use of the entomopathogenic fungal strains disclosed herein with an RNAi trait comprising a silencing construct of one or more polynucleotides of interest resulting in suppression of one or more target pathogen, pest, or insect polypeptides. By "silencing element" is it intended to mean a polynucleotide which when contacted by or ingested by a pest, is capable of reducing or eliminating the level or expression of a target polynucleotide or the polypeptide encoded thereby. The silencing element employed can reduce or eliminate the expression level of the target sequence by influencing the level of the target RNA transcript or, alternatively, by influencing translation and thereby affecting the level of the encoded polypeptide. Silencing elements may include, but are not limited to, a sense suppression element, an antisense suppression element, a double stranded RNA, a siRNA, an amiRNA, a miRNA, or a hairpin suppression element.

In another embodiment, the disclosure relates to the use of the entomopathogenic fungal strains disclosed herein with a composition comprising nucleic acid molecules including silencing elements for targeting the vacuolar ATPase H subunit, useful for controlling a *coleopteran* pest population and infestation as described in US Patent Application Publication 2012/0198586. PCT Publication WO 2012/055982 describes ribonucleic acid (RNA or double stranded RNA) that inhibits or down regulates the expression of a target gene that encodes: an insect ribosomal protein such as the ribosomal protein L19, the ribosomal protein L40 or the ribosomal protein S27A; an insect proteasome subunit such as the Rpn6 protein, the Pros 25, the Rpn2 protein, the proteasome beta 1 subunit protein or the Pros beta 2 protein; an insect β-coatomer of the COPI vesicle, the γ-coatomer of the COPI vesicle, the β'-coatomer protein or the ζ-coatomer of the COPI vesicle; an insect Tetraspanine 2 A protein which is a putative transmembrane domain protein; an insect protein belonging to the actin family such as Actin 5C; an insect ubiquitin-5E protein; an insect Sec23 protein which is a GTPase activator involved in intracellular protein transport; an insect crinkled protein which is an unconventional myosin which is involved in motor activity; an insect crooked neck protein which is involved in the regulation of nuclear alternative mRNA splicing; an insect vacuolar H+-ATPase G-subunit protein and an insect Tbp-1 such as Tat-binding protein. PCT publication WO 2007/035650 describes ribonucleic acid (RNA or double stranded RNA) that inhibits or down regulates the expression of a target gene that encodes Snf7. US Patent Application publication 2011/0054007 describes polynucleotide silencing elements targeting RPS10. US Patent Application publication 2014/0275208 and US2015/0257389 describe polynucleotide silencing elements targeting RyanR and PAT3. PCT publications WO 2016/060911, WO 2016/060912, WO 2016/060913, and WO 2016/060914 describe polynucleotide silencing elements targeting COPI coatomer subunit nucleic acid molecules that confer resistance to *Coleopteran* and *Hemipteran* pests. International Application Number PCT/US2016/037748 describes polynucleotide silencing elements targeting VgR, MAEL, NCLB, and BOULE that control Coloepteran insect pests. US Patent Application Publications 2012/029750, US 20120297501, and 2012/0322660 describe interfering ribonucleic acids (RNA or double stranded RNA) that functions upon uptake by an insect pest species to down-regulate expression of a target gene in said insect pest, wherein the RNA comprises at least one silencing element wherein the silencing element is a region of double-stranded RNA comprising annealed complementary strands, one strand of which comprises or consists of a sequence of nucleotides which is at least partially complementary to a target nucleotide sequence within the target gene. US Patent Application Publication 2012/0164205 describe potential targets for interfering double stranded ribonucleic acids for inhibiting invertebrate pests including: a Chd3 Homologous Sequence, a Beta-Tubulin Homologous Sequence, a 40 kDa V-ATPase Homologous Sequence, a EF1α Homologous Sequence, a 26S Proteosome Subunit p28 Homologous Sequence, a Juvenile Hormone Epoxide Hydrolase Homologous Sequence, a Swelling Dependent Chloride Channel Protein Homologous Sequence, a Glucose-6-Phosphate 1-Dehydrogenase Protein Homologous Sequence, an Act42A Protein Homologous Sequence, a ADP-Ribosylation Factor 1 Homologous Sequence, a Transcription Factor IIB Protein Homologous Sequence, a Chitinase Homologous Sequences, a Ubiquitin Conjugating Enzyme Homologous Sequence, a Glyceraldehyde-3-Phosphate Dehydrogenase Homologous Sequence, an Ubiquitin B Homologous Sequence, a Juvenile Hormone Esterase Homolog, and an Alpha Tubulin Homologous Sequence.

One embodiment of the invention comprises an additional component, which may be a carrier, an adjuvant, a solubilizing agent, a suspending agent, a diluent, an oxygen scavenger, an antioxidant, a food material, an anti-contaminant agent, or combinations thereof.

In another embodiment, the additional component(s) may be required for the application to which the strain or composition is to be utilized. For example, if the strain or composition is to be utilized on, or in, an agricultural product, the additional component(s) may be an agriculturally acceptable carrier, excipient, or diluent. Likewise, if the strain or composition is to be utilized on, or in, a foodstuff the additional component(s) may be an edible carrier, excipient or diluent.

In one aspect, the one or more additional component(s) is a carrier, excipient, or diluent.

"Carriers" or "vehicles" mean materials suitable for compound administration and include any such material known in the art such as, for example, any liquid, gel, solvent, liquid diluent, solubilizer, or the like, which is non-toxic and does not interact with any components of the composition in a deleterious manner.

Examples of nutritionally acceptable carriers include, for example, water, salt solutions, alcohol, silicone, waxes, petroleum jelly, vegetable oils, polyethylene glycols, propylene glycol, liposomes, sugars, gelatin, lactose, amylose, magnesium stearate, talc, surfactants, silicic acid, viscous paraffin, perfume oil, fatty acid monoglycerides and diglycerides, petroethral fatty acid esters, hydroxymethyl-cellulose, polyvinylpyrrolidone, and the like.

Examples of excipients include but are not limited to: microcrystalline cellulose and other celluloses, lactose, sodium citrate, calcium carbonate, dibasic calcium phosphate, glycine, starch, milk sugar, and high molecular weight polyethylene glycols.

Examples of diluents include but are not limited to: water, ethanol, propylene glycol and glycerin, and combinations thereof.

Additional components may be used simultaneously with an entomopathogenic fungal strain and/or a composition disclosed herein (e.g. when they are in admixture together or even when they are delivered by different routes) or sequentially (e.g. they may be delivered by different routes).

An entomopathogenic fungal strain and/or a composition disclosed herein and/or its diluent may also contain chelating agents such as EDTA, citric acid, tartaric acid, etc. Moreover, an entomopathogenic fungal strain and/or a composition disclosed herein and/or its diluent may contain active agents selected from fatty acids esters, such as mono- and diglycerides, non-ionic surfactants, such as polysorbates, phospholipids, etc. An entomopathogenic fungal strain and/or a composition disclosed herein and/or its diluent may also contain emulsifiers, which may enhance the stability of an entomopathogenic fungal strain and/or a composition, especially after dilution.

An entomopathogenic fungal strain and/or a composition disclosed herein may be used in any suitable form, whether when used alone or when present in a composition. An entomopathogenic fungal strain and/or a composition disclosed herein may be formulated in any suitable way to ensure that the composition comprises an active entomopathogenic fungal strain.

An entomopathogenic fungal strain and/or compositions may be in the form of a dry powder that can be sprinkled on or mixed in with a product. Entomopathogenic fungal strains and/or compositions of the embodiments of the invention disclosed herein in the form of a dry powder may include an additive such as microcrystalline cellulose, gum tragacanth, gelatin, starch, lactose, alginic acid, Primojel®, or corn starch (which can be used as a disintegrating agent).

In yet another embodiment, entomopathogenic fungal strains and/or compositions disclosed herein can be a spray-dried fermentate re-suspended in $H_2O$ to a percentage selected from the following: 0.05-1, 1-3, 3-5, 5-7, 7-10, 10-15, 15-20, and greater than 20%. In another embodiment, a clarification step may be performed prior to spray-drying.

In one embodiment, the compositions disclosed herein can comprise a suspension of propagules, such as spores, from the entomopathogenic fungal strains disclosed herein. In one embodiment, the suspension of propagules, such as spores, can be in the range of $1\times10^2$ to $1\times10^{14}$ CFU/ml.

In one embodiment, the compositions disclosed herein can comprise concentrated, dried propagules, such as spores, from the entomopathogenic fungal strains disclosed herein. In one embodiment, the concentrated, dries spores can be in the range of $1\times10^2$ to $1\times10^{14}$ CFU/g.

In one embodiment, entomopathogenic fungal strains and/or entomopathogenic fungal compositions disclosed herein can be applied in wet or partially or completely desiccated form or in slurry, gel, or other form.

In at least some embodiments, entomopathogenic fungal strains and/or compositions can be freeze-dried or lyophilized. In at least some embodiments, entomopathogenic fungal strains and/or entomopathogenic fungal compositions can be mixed with a carrier. The carrier includes but is not limited to whey, maltodextrin, sucrose, dextrose, limestone (calcium carbonate), rice hulls, yeast culture, dried starch, clay, and sodium silico aluminate. However, it is not necessary to freeze-dry the strains before using them. The strains can also be used with or without preservatives and in concentrated, un-concentrated, or diluted form. In one embodiment, the strains can be in the form of a pellet or a biologically pure pellet.

An entomopathogenic fungal strain and/or a composition described herein can be added to one or more carrier. Where used, the carrier(s) and the strains can be added to a ribbon or paddle mixer and mixed for about 15 minutes, although the timing can be increased or decreased. The components are blended such that a uniform mixture of the culture and carrier(s) is produced. The final product is preferably a dry, flowable powder.

In an embodiment, an entomopathogenic fungal strain and/or compositions may be formulated as a liquid, a dry powder, or a granule. The dry powder or granules may be prepared by means known to those skilled in the art, such as, in top-spray fluid bed coater, in a bottom spray Wurster, or by drum granulation (e.g. high sheer granulation), extrusion, pan coating or in a micro-ingredients mixer.

In another embodiment, entomopathogenic fungal strains and/or compositions may be provided as a spray-dried or freeze-dried powder.

In yet another embodiment, the entomopathogenic fungal strains and/or compositions are in a liquid formulation. Such liquid consumption may contain one or more of the following: a buffer, salt, sorbitol, and/or glycerol.

In one embodiment, the entomopathogenic fungal strains and/or compositions disclosed herein may be formulated with at least one physiologically acceptable carrier selected from at least one of maltodextrin, calcined (illite) clay, limestone (calcium carbonate), cyclodextrin, wheat or a wheat component, sucrose, starch, $Na_2SO_4$, Talc, PVA, sorbitol, benzoate, sorbiate, glycerol, sucrose, propylene glycol, 1,3-propane diol, glucose, parabens, sodium chloride, citrate, acetate, phosphate, calcium, metabisulfite, formate and mixtures thereof.

In one embodiment, the entomopathogenic fungal strains and/or compositions disclosed herein may be formulated by encapsulation technology to improve fungal propagule, such as spores, stability and as a way to protect the fungal propagules from seed applied fungicides. In one embodiment the encapsulation technology may comprise a bead polymer for timed release of fungal propagules, such as spores, over time. In one embodiment, the encapsulated entomopathogenic fungal strains and/or entomopathogenic fungal compositions may be applied in a separate application of beads in-furrow to the seeds. In another embodiment, the encapsulated entomopathogenic fungal strains and/or entomopathogenic fungal compositions may be co-applied along with seeds simultaneously.

A coating agent usable for the sustained release microparticles of an encapsulation embodiment may be a substance which is useful for coating the microgranular form with the substance to be supported thereon. Any coating agent which can form a coating difficultly permeable for the supported substance may be used in general, without any particular limitation. For example, higher saturated fatty acid, wax, thermoplastic resin, thermosetting resin and the like may be used.

Examples of useful higher saturated fatty acid include stearic acid, zinc stearate, stearic acid amide and ethylenebis-stearic acid amide; those of wax include synthetic waxes such as polyethylene wax, carbon wax, Hoechst wax, and fatty acid ester; natural waxes such as carnauba wax, bees wax and Japan wax; and petroleum waxes such as paraffin wax and petrolatum. Examples of thermoplastic resin include polyolefins such as polyethylene, polypropylene, polybutene and polystyrene; vinyl polymers such as polyvinyl acetate, polyvinyl chloride, polyvinylidene chloride, polyacrylic acid, polymethacrylic acid, polyacrylate and polymethacrylate; diene polymers such as butadiene polymer, isoprene polymer, chloroprene polymer, butadiene-styrene copolymer, ethylene-propylene-diene copolymer, styrene-isoprene copolymer, MMA-butadiene copolymer and acrylonitrile-butadiene copolymer; polyolefin copolymers such as ethylene-propylene copolymer, butene-ethylene copolymer, butene-propylene copolymer, ethylene-vinyl acetate copolymer, ethylene-acrylic acid copolymer, styreneacrylic acid copolymer, ethylene-methacrylic acid copolymer, ethylene-methacrylic ester copolymer, ethylene-carbon monoxide copolymer, ethylene-vinyl acetate-carbon monoxide copolymer, ethylene-vinyl acetate-vinyl chloride copolymer and ethylene-vinyl acetate-acrylic copolymer; and vinyl chloride copolymers such as vinyl chloride-vinyl acetate copolymer and vinylidene chloride-vinyl chloride copolymer. Examples of thermosetting resin include polyurethane resin, epoxy resin, alkyd resin, unsaturated polyester resin, phenolic resin, urea-melamine resin, urea resin and silicone resin. Of those, thermoplastic acrylic ester resin, butadienestyrene copolymer resin, thermosetting polyurethane resin and epoxy resin are preferred, and among the preferred resins, particularly thermosetting polyurethane resin is preferred. These coating agents can be used either singly or in combination of two or more kinds.

In one embodiment, the entomopathogenic fungal strains, and/or compositions may include a seed, a part of a seed, a plant, or a plant part.

All plants, plant parts, seeds or soil can be treated in accordance with the entomopathogenic fungal strains, compositions, and methods disclosed herein. The compositions disclosed herein can include a plant, a plant part, a seed, a seed part, or soil. The entomopathogenic fungal strains, entomopathogenic fungal compositions, and methods disclosed herein can be applied to the seed, the plant or plant parts, the fruit, or the soil in which the plants grow.

An embodiment relates to a method for reducing plant pathogen, pest, or insect damage to a plant or plant part comprising: (a) treating a seed with an entomopathogenic fungal strain or entomopathogenic fungal composition disclosed herein prior to planting. In another embodiment, the method further comprises: (b) treating a plant part obtained from the seed with an entomopathogenic fungal strain or entomopathogenic fungal composition disclosed herein. The entomopathogenic fungal strain or entomopathogenic fungal composition used in step (a) may be the same or different than the entomopathogenic fungal strain or entomopathogenic fungal composition used in step (b).

An embodiment relates to a method for reducing plant pathogen, pest, or insect damage to a plant or plant part comprising: (a) treating the soil surrounding a seed or plant with an entomopathogenic fungal strain or entomopathogenic fungal composition. In another embodiment, the method further comprises: (b) treating a plant part with an entomopathogenic fungal strain or entomopathogenic fungal composition disclosed herein. The entomopathogenic fungal strain or entomopathogenic fungal composition used in step (a) may be the same or different than the entomopathogenic fungal strain or entomopathogenic fungal composition used in step (b).

An embodiment relates to a method for reducing plant pathogen, pest, or sect damage to a plant or plant part comprising: (a) treating a seed prior to planting with an entomopathogenic fungal strain or composition disclosed herein. In another embodiment, the method further comprises: (b) treating the soil surrounding the seed or plant with an entomopathogenic fungal strain or composition disclosed herein. In still another embodiment, the method further comprises: (c) treating a plant part of a plant produced from the seed with an entomopathogenic fungal strain or composition disclosed herein. The entomopathogenic fungal strain or composition used in step (a) may be the same or different than the entomopathogenic fungal strain or composition used in step (b). The entomopathogenic fungal strain or composition used in step (a) may be the same or different than the entomopathogenic fungal strain or composition used in step (c). The entomopathogenic fungal strain or composition used in step (b) may be the same or different than the entomopathogenic fungal strain or composition used in step (c).

In one embodiment, wild plant species and plant cultivars, or those obtained by conventional biological breeding, such as crossing or protoplast fusion, and parts thereof, can be treated with one or more entomopathogenic fungal strains, compositions and methods disclosed herein. In another embodiment, transgenic plants and plant cultivars obtained by genetic engineering, and plant parts thereof, are treated with one or more entomopathogenic fungal strains, entomopathogenic fungal compositions and methods disclosed herein.

In another embodiment, plants or plant cultivars (obtained by plant biotechnology methods such as genetic engineering) that may be treated according to the strains, compositions and methods disclosed herein are herbicide-tolerant plants, i.e. plants made tolerant to one or more given herbicides. Such plants can be obtained either by genetic modification, or by selection of plants containing a mutation imparting such herbicide tolerance. Herbicide-resistant plants are for example glyphosate-tolerant plants, i.e. plants made tolerant to the herbicide glyphosate or salts thereof. Plants can be made tolerant to glyphosate through different means. For example, glyphosate-tolerant plants can be obtained by transforming the plant with a gene encoding the enzyme 5-enolpyruvylshilcimate-3-phosphate synthase (EPSPS).

Seeds, plants or plant cultivars (obtained by plant biotechnology methods such as genetic engineering) that may also be treated according to the embodiments disclosed herein are insect-resistant genetically modified plants (or transgenic plants), i.e. plants made resistant to attack by certain target insects. Such plants can be obtained by genetic transformation, or by selection of plants containing a mutation imparting such insect resistance.

In another embodiment, seeds, plants or plant cultivars (Obtained by plant biotechnology methods such as genetic engineering) that may be treated according to the disclosure are tolerant to abiotic stresses. Such plants can be obtained by genetic transformation, or by selection of plants containing a mutation imparting such stress resistance.

In another embodiment, seeds, plants or plant cultivars (obtained by plant biotechnology methods such as genetic engineering) that may be treated according to the disclosure are conventionally bred, by mutagenesis, or genetically engineered to contain a combination or stack of valuable traits, including but not limited to, herbicide tolerance, insect resistance, and abiotic stress tolerance. The embodiments disclosed herein also apply to plant varieties which will be developed, or marketed, in the future and which have these genetic traits or traits to be developed in the future.

As used herein, applying an entomopathogenic fungal strain or composition to a seed, a plant, or plant part includes contacting, spraying, coating, misting, and/or applying the seed, plant, or plant part directly and/or indirectly with the entomopathogenic fungal strain or composition. In one embodiment, an entomopathogenic fungal strain or composition may be directly applied as a spray, a rinse, or a powder, or any combination thereof. A contacting step may occur while a seed, a plant or a plant part is being grown, while a plant or a plant part is being fertilized, while a plant or a plant part is being harvested, after a plant or a plant part has been harvested, while a plant or a plant part is being processed, while a plant or a plant part is being packaged, or while a plant or a plant part is being stored in warehouse or on a shelf in a store.

As used herein, a spray refers to a mist of liquid particles that contain an entomopathogenic fungal strain or composition of the present disclosure. In one embodiment, a spray may be applied to a seed, plant, or plant part while a plant or plant part is being grown. In another aspect, a spray may be applied to a seed, plant, or plant part while a seed, plant, or plant part is being fertilized. In another aspect, a spray may be applied to a seed, plant, or plant part while a seed, plant, or plant part is being harvested. In another aspect, a spray may be applied to a seed, plant, or plant part after a seed, plant, or plant part has been harvested. In another aspect, a spray may be applied to a seed, plant, or plant part while a plant or plant part is being processed. In another aspect, a spray may be applied to a seed, plant, or plant part while a seed, plant, or plant part is being packaged. In another aspect, a spray may be applied to a seed, plant, or plant part while a seed, plant, or plant part is being stored.

In another embodiment, an entomopathogenic fungal strain or composition disclosed herein may be applied directly to a seed, plant, or plant part as a rinse. As used herein, a rinse is a liquid containing an entomopathogenic fungal strain or composition disclosed herein. Such a rinse may be poured over a seed, plant or plant part. A plant or plant part may also be immersed or submerged in the rinse, then removed and allowed to dry.

In another embodiment, an entomopathogenic fungal strain or composition may be applied to a seed, plant, or plant part and may cover 50% of the surface area of a plant material. In another embodiment, an entomopathogenic fungal strain or composition may be applied to a plant or plant part and may cover a percentage of the surface area of a plant material from 50% to about 95%, from 60% to about 95%, from 70% to about 95%, from 80% to about 95%, and from 90% to about 95%. In another embodiment, an entomopathogenic fungal strain or a composition disclosed herein may be applied to the environment of a seed, a plant or a plant part and may cover 50% of the surface area of the environment of a seed, a plant or a plant part. In another embodiment, an entomopathogenic fungal strain or a composition may be applied to the environment of a seed, a plant or a plant part and may cover a percentage of the surface area of the environment of a seed, a plant or a plant part from 50% to about 95%, from 60% to about 95%, from 70% to about 95%, from 80% to about 95%, and from 90% to about 95%.

In another aspect, an entomopathogenic fungal strain or composition may cover from about 20% to about 30%, from about 30% to about 40%, from about 40% to about 50%, from about 50% to about 60%, from about 60% to about 70%, from about 70% to about 80%, from about 80% to about 90%, from about 90% to about 95%, from about 95% to about 98%, from about 98% to about 99% or 100% of the surface area of a seed, a plant or a plant part or the environment of a seed, a plant or a plant part.

In another embodiment, an entomopathogenic fungal strain or composition disclosed herein may be applied directly to a seed, a plant or a plant part or the environment of a seed, a plant or a plant part as a powder. As used herein, a powder is a dry or nearly dry bulk solid composed of a large number of very fine particles that may flow freely when shaken or tilted. A dry or nearly dry powder composition disclosed herein preferably contains a low percentage of water, such as, for example, in various aspects, less than 5%, less than 2.5%, or less than 1% by weight.

In another embodiment, an entomopathogenic fungal strain or composition can be applied indirectly to a seed, a plant or a plant part or the environment of a seed, a plant or a plant part. For example, a seed, plant, or plant part having an entomopathogenic fungal strain or composition already applied may be touching a second seed, plant, or plant part so that an entomopathogenic fungal strain or composition rubs off on a second seed, plant, or plant part. In a further aspect, an entomopathogenic fungal strain or composition may be applied using an applicator. In various aspects, an applicator may include, but is not limited to, a syringe, a sponge, a paper towel, or a cloth, or any combination thereof.

A contacting step may occur while a plant material is being grown, while a seed, plant, or plant part is being fertilized, while a plant or plant part is being harvested, after a seed, plant, or plant part has been harvested, while a plant or plant part is being processed, while a plant or plant part is being packaged, or while a plant or plant part is being stored in a warehouse.

In another embodiment, an entomopathogenic fungal strain or composition disclosed herein may be a colloidal dispersion. A colloidal dispersion is a type of chemical mixture where one substance is dispersed evenly throughout another. Particles of the dispersed substance are only suspended in the mixture, unlike a solution, where they are completely dissolved within. This occurs because the particles in a colloidal dispersion are larger than in a solution—small enough to be dispersed evenly and maintain a homogenous appearance, but large enough to scatter light and not dissolve. Colloidal dispersions are an intermediate between homogeneous and heterogeneous mixtures and are sometimes classified as either “homogeneous” or “heterogeneous” based upon their appearance.

In one embodiment, the entomopathogenic fungal strains, compositions, and methods disclosed herein are suitable for use with a seed. In another embodiment, the entomopathogenic fungal strains, compositions, and methods disclosed herein are suitable for use with a seed of one or more of any of the plants recited previously.

In still another embodiment, entomopathogenic fungal strains, compositions and methods disclosed herein can be used to treat transgenic or genetically modified seed. The heterologous gene in transgenic seed can originate, for example, from microorganisms of the species *Bacillus, Rhizobium, Pseuclonionas, Serratia, Trichoderma, Clavibacter, Glomus or Gliocladium.*

In one embodiment, a seed is treated in a state in which it is sufficiently stable so that the treatment does not cause any damage. In general, treatment of a seed may take place at any point in time between harvesting and sowing. In one embodiment, a seed used is separated from the plant and freed from cobs, shells, stalks, coats, hairs or the flesh of the fruits. Thus, it is possible to use, for example, a seed which has been harvested, cleaned and dried. Alternatively, it is also possible to use a seed which, after drying, has been treated, for example, with water and then dried again.

In one embodiment, seed is treated with the entomopathogenic fungal strains, compositions, and methods disclosed herein in such a way that the germination of a seed is not adversely affected, or that the resulting plant is not damaged.

In one embodiment, entomopathogenic fungal strains and compositions disclosed herein can be applied directly to a seed. For example, entomopathogenic fungal strains, compositions and methods disclosed herein can be applied without additional components and without having been diluted.

In another embodiment, entomopathogenic fungal strains, and entomopathogenic fungal compositions disclosed herein are applied to a seed in the form of a suitable formulation. Suitable formulations and methods for the treatment of seed are known to the person skilled in the art and are described, for example, in the following documents: U.S. Pat. No. 4,272,417 A, U.S. Pat. No. 4,245,432 A, U.S. Pat. No. 4,808,430 A, U.S. Pat. No. 5,876,739 A, US 2003/0176428 A1, WO 2002/080675 A1, WO 2002/028186 A2.

The entomopathogenic fungal strains and compositions disclosed herein can be converted into customary seed dressing formulations, such as solutions, emulsions, suspensions, powders, foams, slurries or other coating materials for seed, and also ULV formulations. These formulations are prepared in a known manner by mixing the entomopathogenic fungal strains and disclosed herein with customary additives, such as, for example, customary extenders and also solvents or diluents, colorants, wetting agents, dispersants, emulsifiers, defoamers, preservatives, secondary thickeners, adhesives, gibberellins and water as well.

In another embodiment, suitable colorants that may be present in a seed dressing formulation include all colorants customary for such purposes. Use may be made both of pigments, of sparing solubility in water, and of dyes, which are soluble in water. Examples that may be mentioned include the colorants known under the designations Rhodamine B, C.I. Pigment Red 112, and C.I. Solvent Red 1.

In another embodiment, suitable wetting agents that may be present in a seed dressing formulation include all substances that promote wetting and are customary in the formulation of active agrochemical substances. With preference it is possible to use alkylnaphthalene-sulphonates, such as diisopropyl- or diisobutylnaphthalene-sulphonates.

In still another embodiment, suitable dispersants and/or emulsifiers that may be present in a seed dressing formulation include all nonionic, anionic, and cationic dispersants that are customary in the formulation of active agrochemical substances. In one embodiment, nonionic or anionic dispersants or mixtures of nonionic or anionic dispersants can be used. In one embodiment, nonionic dispersants include but are not limited to ethylene oxide-propylene oxide block polymers, alkylphenol polyglycol ethers, and tristyrylphenol polyglycol ethers, and their phosphated or sulphated derivatives.

In still another embodiment, defoamers that may be present in a seed dressing formulation to be used according to the embodiments of the invention include all foam-inhibiting compounds that are customary in the formulation of agrochemically active compounds including but not limited to silicone defoamers, magnesium stearate, silicone emulsions, long-chain alcohols, fatty acids and their salts and also organofluorine compounds and mixtures thereof.

In still another embodiment, secondary thickeners that may be present in a seed dressing formulation include all compounds which can be used for such purposes in agrochemical compositions, including but not limited to cellulose derivatives, acrylic acid derivatives, polysaccharides, such as xanthan gum or Veegum, modified clays, phyllosilicates, such as attapulgite and bentonite, and also finely divided silicic acids. Suitable adhesives that may be present in a seed dressing formulation to be used may include all customary binders which can be used in seed dressings. Polyvinylpyrrolidone, polyvinyl acetate, polyvinyl alcohol and tylose may be mentioned as being preferred.

In yet another embodiment, seed dressing formulations may be used directly or after dilution with water beforehand to treat seed of any of a very wide variety of types. The seed dressing formulations or their dilute preparations may also be used to dress seed of transgenic plants. In this context, synergistic effects may also arise in interaction with the substances formed by expression.

Suitable mixing equipment for treating seed with a seed dressing formulation or the preparations prepared from them by adding water includes all mixing equipment that can commonly be used for dressing. The specific procedure adopted when dressing comprises introducing the seed into a mixer, adding the particular desired amount of seed dressing formulation, either as it is or following dilution with water beforehand, and carrying out mixing until the formulation is uniformly distributed on the seed. Optionally, a drying operation follows.

In various embodiments, one or more entomopathogenic fungal strains, entomopathogenic fungal compositions or entomopathogenic fungal formulations can be added to the plant, plant part, and/or seed at a rate of about 10 to $1\times10^{14}$ colony forming units (cfu) per seed, including about $1\times10^{3}$ cfu/seed, or about $1\times10^{4}$ cfu/seed, $1\times10^{5}$ cfu/seed, or about $1\times10^{6}$ cfu/seed, or about $1\times10^{7}$ cfu/seed, or about $1\times10^{8}$ cut/seed, or about $1\times10^{9}$ cfu/seed, or about $1\times10^{10}$ cfu/seed, or about $1\times10^{11}$ cfu/seed, or about $1\times10^{12}$ cfu/seed, or about $1\times10^{13}$ cfu/seed including about $1\times10^{3}$ to $1\times10^{8}$ cfu/seed about $1\times10^{3}$ to $1\times10^{7}$ cfu/seed, about $1\times10^{3}$ to $1\times10^{5}$ cfu/seed, about $1\times10^{3}$ to $1\times10^{6}$ cfu/seed, about $1\times10^{3}$ to $1\times10^{4}$ cfu/seed, about $1\times10^{3}$ to $1\times10^{9}$ cfu/seed, about $1\times10^{3}$ to $1\times10^{10}$ cfu/seed, about $1\times10^{3}$ to $1\times10^{11}$ cfu/seed, about $1\times10^{3}$ to $1\times10^{12}$ cfu/seed, about $1\times10^{3}$ to $1\times10^{13}$ cfu/seed, about $1\times10^{4}$ to $1\times10^{8}$ cfu/seed about $1\times10^{4}$ to $1\times10^{7}$ cfu/seed, about $1\times10^{4}$ to $1\times10^{5}$ cfu/seed, about $1\times10^{4}$ to $1\times10^{6}$ cfu/seed, about $1\times10^{4}$ to $1\times10^{9}$ cfu/seed, about $1\times10^{4}$ to $1\times10^{10}$ cfu/seed, about $1\times10^{11}$ to $1\times10^{9}$ cfu/seed, about $1\times10^{4}$ to $1\times10^{12}$ cfu/seed about $1\times10^{4}$ to $1\times10^{13}$ cfu/seed, about $1\times10^{5}$ to $1\times10^{7}$ cfu/per seed, about $1\times10^{5}$ to $1\times10^{6}$ cfu/per seed, about $1\times10^{5}$ to $1\times10^{8}$ cfu/per seed, about $1\times10^{5}$ to $1\times10^{9}$ cfu/per seed, about $1\times10^{5}$ to $1\times10^{10}$ cfu/per seed, about $1\times10^{5}$ to $1\times10^{11}$ cfu/per seed, about $1\times10^{5}$ to $1\times10^{12}$ cfu/per seed, about $1\times10^{5}$ to $1\times10^{13}$ cfu/per seed, about $1\times10^{6}$ to $1\times10^{8}$ cfu/per seed, about $1\times10^{6}$ to $1\times10^{7}$ cfu/per seed, about $1\times10^{6}$ to $1\times10^{9}$ cfu/per seed, about $1\times10^{6}$ to $1\times10^{10}$ cfu/per seed, about $1\times10^{6}$ to $1\times10^{11}$ cfu/per seed, about $1\times10^{6}$ to $1\times10^{12}$ cfu/per seed, about $1\times10^{6}$ to $1\times10^{13}$ cfu/per seed, about $1\times10^{7}$ to $1\times10^{8}$ cfu/per seed, about $1\times10^{7}$ to $1\times10^{9}$ cfu/per seed, about $1\times10^{7}$ to $1\times10^{10}$ cfu/per seed, about $1\times10^{7}$ to $1\times10^{11}$ cfu/per seed, about $1\times10^{7}$ to $1\times10^{12}$ cfu/per seed, about $1\times10^{7}$ to $1\times10^{13}$ cfu/per seed, about $1\times10^{8}$ to $1\times10^{9}$ cfu/per seed, about $1\times10^{8}$ to $1\times10^{10}$ cfu/per seed, about $1\times10^{8}$ to $1\times10^{11}$ cfu/per seed, about $1\times10^{8}$ to $1\times10^{12}$ cfu/per seed, about $1\times10^{8}$ to $1\times10^{13}$ du/per seed, about $1\times10^{9}$ to $1\times10^{10}$ cfu/per seed, about $1\times10^{9}$ to $1\times10^{11}$ cfu/per seed, about $1\times10^{9}$ to $1\times10^{12}$ cfu/per seed, about $1\times10^{9}$ to $1\times10^{13}$ cfu/per seed, about $1\times10^{10}$ to $1\times10^{11}$ cfu/per seed, about $1\times10^{10}$ to $1\times10^{12}$ cfu/per seed, about $1\times10^{10}$ to $1\times10^{13}$ cfu/per seed, about $1\times10^{111}$ to $1\times10^{12}$ cfu/per seed, about $1\times10^{11}$ to $1\times10^{13}$ cfu/per seed, and about $1\times10^{12}$ to $1\times10^{13}$ cfu/per seed. As used herein, the tem "colony forming unit" or "cfu" is a unit containing entomopathogen fungal structures capable of growing and producing a colony in favorable conditions. The cfu count serves as an estimate of the number of viable structures or cells in a sample.

In one embodiment, entomopathogenic fungal strains and compositions can be formulated as a liquid seed treatment. The seed treatment comprises at least one entomopathogenic fungal strain or composition. Seeds may be substantially uniformly coated with one or more layers of an entomopathogenic fungus or composition, using conventional methods of mixing, spraying or a combination thereof. Application may be done using equipment that accurately, safely, and efficiently applies seed treatment products to seeds. Such equipment uses various types of coating technology such as rotary coaters, drum coaters, fluidized bed techniques, spouted beds, rotary mists or a combination thereof.

In one embodiment, the application is done via either a spinning "atomizer" disk or a spray nozzle that evenly distributes the seed treatment onto the seed as it moves through the spray pattern. In yet another embodiment, a seed is then mixed or tumbled for an additional period of time to achieve additional treatment distribution and drying. Seeds may be primed or unprimed before coating with the inventive compositions to increase the uniformity of germination and emergence. In an alternative embodiment, a dry powder composition can be metered onto the moving seed.

In still another embodiment, a seed may be coated via a continuous or batch coating process. In a continuous coating process, continuous flow equipment simultaneously meters both the seed flow and the seed treatment products. A slide gate, cone and orifice, seed wheel, or weight device (belt or divertert regulates seed flow. Once the seed flow rate through treating equipment is determined, the flow rate of the seed treatment is calibrated to the seed flow rate in order to deliver the desired dose to the seed as it flows through the seed treating equipment. Additionally, a computer system may monitor the seed input to the coating machine, thereby maintaining a constant flow of the appropriate amount of seed.

In a batch coating process, batch treating equipment weighs out a prescribed amount of seed and places the seed into a closed treating chamber or bowl where the corresponding of seed treatment is then applied. The seed and seed treatment are then mixed to achieve a substantially uniform coating on each seed. This batch is then dumped out of the treating chamber in preparation for the treatment of the next batch. With computer control systems, this batch process is automated enabling it to continuously repeat the batch treating process.

A variety of additives can be added to a seed treatment. Binders can be added and include those composed preferably of an adhesive polymer that can be natural or synthetic without phytotoxic effect on the seed to be coated. A variety of colorants may be employed, including organic chromophores classified as nitroso, nitro, azo, including monoazo, bisazo, and polyazo, diphenylmethane, triarylmethane, xanthene, methane, acridine, thiazole, thiazine, indamine, indophenol, azine, oxazine, anthraquinone, and phthalocyanine. Other additives that can be added include trace nutrients such as salts of iron, manganese, boron, copper, cobalt, molybdenum, and zinc. A polymer or other dust control agent can be applied to retain the treatment on the seed surface.

Other conventional seed treatment additives include, but are not limited to, coating agents, wetting agents, buffering agents, and polysaccharides. At least one agriculturally acceptable carrier can be added to the seed treatment formulation such as water, solids or dry powders. The dry powders can be derived from a variety of materials such as wood barks, calcium carbonate, gypsum, vermiculite, talc, humus, activated charcoal, and various phosphorous compounds.

In one embodiment, a seed coating comprises at least one filler, which is an organic or inorganic, natural or synthetic component with which the entomopathogenic fungal strains and compositions thereof are combined to facilitate its application onto the seed. In one embodiment, the filler is an inert solid such as clays, natural or synthetic silicates, silica, resins, waxes, solid fertilizers (for example ammonium salts), natural soil minerals, such as kaolins, clays, talc, lime, quartz, attapulgite, montmorillonite, bentonite, or diatomaceous earths, or synthetic minerals, such as silica, alumina, or silicates, in particular aluminum or magnesium silicates.

In one embodiment, the entomopathogenic fungal strains and/or compositions disclosed herein may be formulated by encapsulation technology to improve fungal spore stability and as a way to protect the fungal spores from seed applied fungicides. In one embodiment the encapsulation technology may comprise a bead polymer for timed release of fungal spores over time. In one embodiment, the encapsulation technology may comprise a zeolite material. In one embodiment, the encapsulated entomopathogenic fungal strains and/or entomopathogenic fungal compositions may be applied in a separate application of beads in-furrow to the seeds. In another embodiment, the encapsulated entomopathogenic fungal strains and/or entomopathogenic fungal compositions may be co-applied along with seeds simultaneously.

Insect resistance management (IRM) is the term used to describe practices aimed at reducing the potential for insect pests to become resistant to an insect management tactic. Maintenance of Bt (*Bacillus thuringiensis*) derived pesticidal proteins, other pesticidal proteins, a chemical, an entomopathogenic biological agent, or other biologicals, IRM is of great importance because of the threat insect resistance poses to the future use of pesticidal plant-incorporated protectants and insecticidal trait technology as a whole. Specific IRM strategies, such as the refuge strategy, mitigate insect resistance to specific insecticidal proteins produced in corn, soybean, cotton, and other crops. However, such strategies result in portions of crops being left susceptible to one or more pests in order to ensure that non-resistant insects develop and become available to mate with any resistant pests produced in protected crops. Accordingly, from a farmer/producer's perspective, it is highly desirable to have as small a refuge as possible and yet still manage insect resistance, in order that the greatest yield be obtained while still maintaining the efficacy of the pest control method used, whether Bt, a different pesticidal protein, a chemical, an entomopathogenic biological agent or other biologicals, some other method, or combinations thereof.

An often used IRM strategy is the planting of a refuge (a portion of the total acreage using non-Bt/pesticidal trait seed), as it is commonly-believed that this will delay the development of insect resistance to pesticidal traits by maintaining insect susceptibility. The theoretical basis of the refuge strategy for delaying resistance hinges on the assumption that the frequency and recessiveness of insect resistance is inversely proportional to pest susceptibility; resistance will be rare and recessive only when pests are very susceptible to the toxin, and conversely resistance will be more frequent and less recessive when pests are not very susceptible. Furthermore, the strategy assumes that resistance to an insecticidal trait is recessive and is conferred by a single locus with two alleles resulting in three genotypes: susceptible homozygotes (SS), heterozygotes (RS), and resistant homozygotes (RR). It also assumes that there will be a low initial resistance allele frequency and that there will be extensive random mating between resistant and susceptible adults. Under ideal circumstances, only rare RR individuals will survive a pesticidal toxin produced by the crop. Both SS and RS individuals will be susceptible to the pesticidal toxin. A structured refuge is a non-Bt/insecticidal trait portion of a grower's field or set of fields that provides for the production of susceptible (SS) insects that may randomly mate with rare resistant (RR) insects surviving the insecticidal trait crop, which may be a Bt trait crop, to produce susceptible RS heterozygotes that will be killed by the Bt/insecticidal trait crop. An integrated refuge is a certain portion of randomly planted non-Bt/insecticidal trait portion of a grower's field or set of fields that provides for the production of susceptible (SS) insects that may randomly mate with rare resistant (RR) insects surviving the insecticidal trait crop to produce susceptible RS heterozygotes that will be killed by the pesticidal trait crop. Each refuge strategy will remove resistant (R) alleles from the insect populations and delay the evolution of resistance.

Another strategy to reduce the need for refuge is the pyramiding of traits with different modes of action against a target insect pest. For example, Bt toxins that have different modes of action pyramided in one transgenic plant are able to have reduced refuge requirements due to reduced resistance risk. Different modes of action in a pyramid combination also extends the durability of each trait, as resistance is slower to develop to each trait.

Currently, the size, placement, and management of the refuge are often considered critical to the success of refuge strategies to mitigate insect resistance to the Bt/pesticidal trait produced in corn, cotton, soybean, and other crops. Because of the decrease in yield in refuge planting areas, some farmers choose to eschew the refuge requirements, and others do not follow the size and/or placement requirements. These issues result in either no refuge or a less effective refuge, and a corresponding risk of the increase in the development of resistance pests.

Accordingly, there remains a need for methods for managing pest resistance in a plot of pest resistant crop plants. It would be useful to provide an improved method for the protection of plants, especially corn or other crop plants, from feeding damage by pests. It would be particularly useful if such a method would reduce the required application rate of conventional chemical pesticides, and also if it would limit the number of separate field operations that were required for crop planting and cultivation. In addition, it would be useful to have a method of deploying a biocontrol agent that increases the durability of an insecticidal trait or increases the efficacy of many resistance management strategies.

One embodiment relates to a method of reducing or preventing the development of resistance to a plant insecticidal/pesticidal composition of a pest in a population comprising providing a plant protection composition, such as a Bt pesticidal protein, a transgenic pesticidal protein, other pesticidal proteins, chemical pesticides, or pesticidal biological entomopathogens to a seed, a plant, a plant part, or a planted area. Another embodiment relates to a method of reducing or preventing the resistance to a plant insecticidal trait comprising providing a composition comprising a plant insecticidal trait and an entomopathogenic fungal strain described herein. A further embodiment relates to a method of reducing or preventing the resistance to a plant *Coleopteran* insecticidal trait comprising providing a composition comprising a plant *Coleopteran* insecticidal trait and an entomopathogenic fungal strain and/or composition described herein. Another embodiment relates to a method of reducing or preventing the resistance to a plant *Diabrotica virgifera virgifera* insecticidal trait comprising providing a plant *Diabrotica virgifera virgifera* insecticidal trait and an entomopathogenic fungal strain and/or composition described herein. In certain embodiments, the insecticidal trait comprises a Bt trait, a non-Bt trait, or an RNAi trait.

A further embodiment relates to a method of increasing the durability of plant pest compositions comprising providing a plant protection composition to a seed, a plant or planted area, and providing the entomopathogenic fungal strains, compositions, and/or methods described herein to the seed, plant, or planted area, wherein the entomopathogenic fungal strains, compositions, and/or methods described herein have a different mode of action than the plant protection composition.

In a still further embodiment, the refuge required may be reduced or eliminated by the presence of entomopathogenic fungal strains, compositions, and/or methods described herein applied to the non-refuge plants. In another embodiment, the refuge may include the entomopathogenic fungal strains, compositions, and/or methods described herein as a spray, bait, or as a different mode of action.

In one embodiment of the invention, a composition comprises a fungal entomopathogen and a non-Bt insecticidal trait increases resistance to a pathogen, pest, or insect. In another embodiment, the fungal entomopathogen is selected from the group consisting of: *Metarhizium robertsii* 15013-1, *Metarhizium robertsii* 23013-3, and *Metarhizium anisopliae* 3213-1. In another embodiment, the non-Bt insecticidal trait comprises a plant-derived insecticidal protein, a bacterial/archeal-derived insecticidal protein not from a Bt (such as a *Pseudomonas* insecticidal protein), an animal-derived insecticidal protein, or a silencing element. In another embodiment of the invention, a composition comprising a fungal entomopathogen and a non-Bt insecticidal trait increases durability of the non-Bt insecticidal trait. In another embodiment, the non-Bt insecticidal trait comprises a PIP-72 polypeptide of PCT Serial Number PCT/US14/55128. In another embodiment, the non-Bt insecticidal trait comprises a polynucleotide silencing elements targeting RyanR, HP2, or PAT3 (US Patent Application publication 2014/0275208 and US2015/0257389). In another embodiment, the non-Bt insecticidal trait comprises a polynucleotide silencing elements targeting RyanR (US Patent Application publication 2014/0275208) and a PIP-72 polypeptide of PCT Serial Number PCT/US14/55128.

In a further embodiment of the invention, a composition that increases resistance to a pathogen, a pest, or an insect comprises a fungal entomopathogen, such as entomopathogenic fungal strain disclosed herein, and a Bt insecticidal trait that increases resistance to a pathogen, pest, or insect. A Bt insecticidal trait may have activity against *Coleopteran* plant pests, such as *Diabrotica virgifera virgifera*. The compositions disclosed herein may provide to a plant or plant part additive or synergistic resistance to a pathogen, pest, or insect plant in combination with a Bt insecticidal trait. In one embodiment, a composition comprises a fungal entomopathogen and a Bt insecticidal trait, wherein the Bt insecticidal trait comprises a Cry3B toxin disclosed in U.S. Pat. Nos. 8,101,826, 6,551,962, 6,586,365, 6,593,273, and PCT Publication WO 2000/011185, a mCry3B toxin disclosed in U.S. Pat. Nos. 8,269,069, and 8,513,492, a mCry3A toxin disclosed in U.S. Pat. Nos. 8,269,069, 7,276,583 and 8,759,620, or a Cry34/35 toxin disclosed in U.S. Pat. Nos. 7,309,785, 7,524,810, 7,985,893, 7,939,651 and 6,548,291, and transgenic events containing these Bt insecticidal toxins and other *Coleopteran* active Bt insecticidal traits for example, event MON863 disclosed in U.S. Pat. No. 7,705,216, event MIR604 disclosed in U.S. Pat. No. 8,884,102, event 5307 disclosed in U.S. Pat. No. 9,133,474, event DAS-59122 disclosed in U.S. Pat. No. 7,875,429, event DP-4114 disclosed in U.S. Pat. No. 8,575,434, event MON 87411 disclosed in US Published Patent Application Number 2013/0340111, and event MON88017 disclosed in U.S. Pat. No. 8,686,230 all of which are incorporated herein by reference.

The entomopathogenic fungal strains, entomopathogenic fungal compositions, and methods will be further understood by reference to the following non-limiting examples. The following Examples are provided for illustrative purposes only. The Examples are included solely to aid in a more complete understanding of the described embodiments of the invention. The Examples do not limit the scope of the embodiments of the invention described or claimed.

Example 1

Bioassay Methodology

Laboratory bioassays were conducted using purified single spore cultures of entomopathogenic fungi to identify strains infective against *Diabrotica virgifera virgifera*. Second instar *D. virgifera virgifera* were submerged a $1\times10^7$/ml suspension of each fungal strain for 1-2 minutes and transferred to Petri dishes with wet filter paper for 24 hrs. Second instar *D. virgifera virgifera* were also submerged in 0.01% Tween 80 solution (Untreated Control) as well as in a $1\times10^7$/ml suspension of a *Beauveria* spp. isolate which originated from an infected *D. virgifera virgifera* and previously shown in the laboratory to be infective (Positive Control). The positive and untreated control treatments served to confirm the validity of each bioassay. A bioassay was considered valid if there were no infected larvae in the untreated control and infected larvae in the positive control. After 24 hrs, larvae were aseptically transferred to Petri plates containing wet filter paper and three coleoptile stage corn seedlings. All fungal strains were screened in triplicate with 10 larvae per replicate. Petri dishes containing larvae and corn seedlings were incubated for 14 days at 25° C. after which time larvae were observed for fungal infection. Fungal infection was confirmed by the presence of conidia on the surface of the cadavers (Table 1).

TABLE 1

| Bioassay | Strain | % Infected CRW Larvae |
|---|---|---|
| 1 | 3213-1 | 50 |
| 1 | Negative Control | 0 |
| 2 | 23013-3 | 26.67 |
| 2 | 15013-1 | 33.33 |
| 2 | Negative Control | 0 |

commercial potting soil and topsoil at a rate equivalent to a field application of $2\times10^{13}$ spores/acre. A negative control treatment consisted of soil not amended with fungal spores. The experiment was a complete factorial design with two factors (fungal strain and germplasm). Seed used consisted of a pre-commercial DuPont Pioneer corn hybrid either with an insecticidal trait (DP-4114, PCT/US10/60818) or wild type plant (untraited) of the same genetic background without a insecticidal trait with activity against *D. virgifera virgifera*. Fifteen individual hybrid corn seed (of each type) were planted into 3.78 L plastic pots and maintained in the greenhouse (80° F., 15:9 L:D) and watered as needed. When the plants reached the V2 leaf stage they were infested with 100 non-diapausing *D. virgifera virgifera* eggs. Plants were monitored daily and the assay ended 14 days after the appearance of the first beetle. The number of adult *D. virgifera virgifera* that emerged from each pot was determined in the GH in a similar manner as described by Meihls et al. (2008) *PNAS* 105: 19177-19182. In those bioassays were adult emergence was not quantified; the assay was evaluated at first beetle emergence. At the conclusion of the assay, the plants were severed above the soil line and the total number of adults present counted. The root ball was then washed and the node-injury-score (CRWNIS) determined (Oleson et al. 2005, *Journal of Economic Entomology* 98: 1-8.) (Table 2).

TABLE 2

| GH BIOASSAY # | STRAIN | WT CRWNIS SCORE* | DP-4114 CRWNIS SCORE* | WT ADULT EMERGENCE* | DP-4114 ADULT EMERGENCE* |
|---|---|---|---|---|---|
| 1 | 15013-1 | 0.90a | 0.15a | 8.93b | 3.88b |
| 1 | Negative Control | 1.89b | 0.62b | 21.87a | 8.68a |
| 2 | 23013-3 | 0.30a | 0.05a | 1.32a | 1.74a |
| 2 | Negative Control | 0.78b | 0.20b | 4.84b | 8.09b |
| 3 | 3213-1 | 0.85a | 0.17a | N/A | N/A |
| 3 | Negative Control | 1.68b | 0.41b | N/A | N/A |

*Pair-wise comparisons were made comparing each fungal strain to the negative control given each genotype. A Dunnett multiplicity adjustment was used and adjusted p-values were considered statistically significant if less than 0.05. Means from the same GH bioassay with different letters ("a" or "b") (CRWNIS or Adult Emergence) within a corn hybrid genotype (WT or DP-4114) are significantly different ($P < 0.05$).

Bioassay Results

The results of the laboratory bioassay demonstrated that the strains 15013-1, 23013-3 and 3213-1 were infective against second instar *D. virgifera virgifera*. The bioassays were performed at a discriminating dose which exposed the larvae to spore concentration that allowed for the identification of highly infective strains, while those strains that were not highly infective against *D. virgifera virgifera* did not result in, or had very low levels of, larval infection. The positive control resulted in larval infection in each of the bioassays reported and the negative control resulted in no larval infection.

Example 2

Soil Incorporation Bioassay Methodology

Whole plant greenhouse bioassays were conducted of the most efficacious entomopathogenic fungal strains identified in the laboratory bioassays. Fungal strains were incorporated immediately prior to planting into a 50:50 blend of a Statistical Analysis Root damage as measured by CRWNIS was analyzed separately for each assay run, using the MIXED procedure in SAS software version number 9.4 (SAS Institute Inc., 100 SAS Campus Drive, Cary, N.C. 27513, USA). In order to better meet model assumptions, CRWINS observed values were transformed, using a square root transformation, prior to analysis.

The model used can be specified:

$$y=b+t+g+t*g+\epsilon$$

where y denotes the response, b denotes block/rep, t denotes the strain treatment, g denotes the genotype, and $\epsilon$ denotes plant-to-plant residual error variance. Treatment and genotype were considered to be fixed effects. All other effects were considered independent normally distributed random variables with means of zero.

Best linear unbiased estimates were reported for each combination of treatment and genotype, following back transformation (i.e., $\hat{y}^2$). Pair-wise comparisons were made comparing each fungal treatment to the check given each genotype. A Dunnett multiplicity adjustment was used and adjusted p-values were considered statistically significant if less than 0.05 beetle emergence data were analyzed separately for each run, using the GLIMMIX procedure in SAS software version number 9.4 (SAS Institute Inc., 100 SAS Campus Drive, Cary, N.C. 27513, USA). A generalized linear mixed model was fit to the data assuming a Poisson distribution of the emergence counts and a log link function.

The linear predictor used can be specified:

$$\eta=b+t+g+t*g+p$$

where $\eta$ denotes the log of the count of emerged beetles, b denotes block/rep, t denotes the strain treatment, g denotes the genotype, and p denotes plant. Treatment and genotype were considered to be fixed effects. All other effects were considered independent normally distributed random variables with means of zero.

Estimates of counts for each treatment by genotype combination were reported on the inverse link scale ($e^{\eta}$). Pairwise comparisons were made comparing each fungal strain to the check given each genotype. A Dunnett multiplicity adjustment was used and adjusted p-values were considered statistically significant if less than 0.05. Means from the same GH bioassay with different letters (CRWNIS or Adult Emergence) within a corn hybrid genotype (WT or DP-4114) are significantly different (P<0.05).

Soil Incorporation Bioassay Results

All entomopathogenic fungal strains evaluated in greenhouse bioassays 1, 2 and 3 significantly reduced the amount of root damage on both genotypes of hybrid corn evaluated. The efficacy provided by each of the entomopathogenic fungi when incorporated at planting was additive with no significant interaction in terms of insect efficacy when used with or without an insecticidal trait. In bioassays 1 and 2 where adult beetle counts were determined, both strains when incorporated into the soil at planting significantly reduced the number of adult *D. virgifera virgifera* that emerged from both hybrid corn genotypes with no significant interaction observed. The use of these fungal strains provided significant level of root protection and reductions in adult emergence as a result of direct mortality against *D. virgifera virgifera* indicating that these fungi are important new tools for use in the development of integrated pest management programs against this insect. In one aspect, the strains may be used to increase the durability of an insecticidal trait.

Example 3

Whole plant greenhouse bioassays were conducted using strain 15013-1 as a biological seed treatment for control of *D. virgifera virgifera*. Fungal spores were applied to hybrid corn seed in the laboratory immediately prior to planting into a 50:50 blend of a commercial potting soil and topsoil. Fungal spores were suspended in a 10% gum arabic solution (to facilitate sticking the spores to the seed) in which naked corn seeds were submerged for 1-2 minutes. The seed treatment doses evaluated were $1\times10^4$, $1\times10^5$ and $1\times10^6$ CFUs/seed. A negative control treatment consisted of seed not treated with fungal spores and dipped in a 10% gum arabic solution alone. The experiment was a complete factorial design with two factors (seed treatment and germplasm). Seed used consisted of a pre-commercial DuPont Pioneer corn hybrid either with an insecticidal trait (DP-4114, PCT/US10/60818) or wild type plant of the same genetic background without an insecticidal trait with activity against *D. virgifera virgifera*. Fifteen individual hybrid corn seed (of each type) were planted into 3.78 L plastic pots and maintained in the greenhouse (80° F., 15:9 L:D) and watered as needed. When the plants reached the V2 leaf stage they were infested with 100 non-diapausing *D. virgifera virgifera* eggs. Plants were monitored daily and the assay ended 14 days after the appearance of the first beetle. The number of adult *D. virgifera virgifera* that emerged from each pot was determined in the GH in a similar manner as described by Meihls et al. (2008) *PNAS* 105: 19177-19182. In those bioassays were adult emergence was not quantified; the assay was evaluated at first beetle emergence. The plants were severed above the soil line the root ball was then washed and the node-injury-score (CRWNIS) determined (Oleson et al. 2005, *Journal of Economic Entomology* 98: 1-8.) (Table 3). Predicted CRWNIS score was calculated as in Example 2.

TABLE 3

| STRAIN | WT CRWNIS SCORE | DP-4114 CRWNIS SCORE |
|---|---|---|
| 15013-1 @ ~1 × $10^4$/seed | 0.53 | 0.41 |
| 15013-1 @ ~1 × $10^5$/seed | 0.57 | 0.39 |
| 15013-1 @ ~1 × $10^6$/seed | 0.49 | 0.35 |
| Untreated Control | 0.63 | 0.34 |

Results

Seed treatment application of strain 15013-1 to naked corn seed generally lowered the amount of root damage caused by *D. virgifera virgifera* (Table 3). The amount of *D. virgifera virgifera* feeding in this greenhouse assay was light. As a result, the amount of insect feeding was highest on the corn genotype without a PIP which allowed for the impact of fungal seed treatment to be the most apparent. The experimental application of fungal spores to corn seed in this example using 10% gum arabic and the resulting performance compared to the superior performance observed in Example 6 (Table 7) are likely influenced by the use of commercial seed treatment equipment and commercial polymers which result in more uniform and consistent application of the fungal spores to the corn seed.

Example 4

Whole plant greenhouse bioassays were conducted using strain 15013-1 as a biological seed treatment for control of *D. virgifera virgifera* alone and in combination with commercial seed applied chemistry. Hybrid corn seed was first treated with a standard commercially available seed application of insecticides and fungicides and allowed to dry. Fungal spores were then applied immediately prior to planting into a 50:50 blend of a commercial potting soil and topsoil. Fungal spores were suspended in a 10% gum arabic solution (to facilitate sticking the spores to the seed) in which corn seeds were submerged for 1-2 minutes. The seed treatment doses evaluated were $1\times10^7$ and $1\times10^8$ CFUs/seed. Negative control treatment consisted of seed treated with 10% gum arabic alone or seed applied chemistry and 10% gum arabic. The experiment was a complete factorial design with two factors (seed treatment and germplasm). Seed used consisted of a pre-commercial DuPont Pioneer corn hybrid either with an insecticidal trait (DP-4114, PCT/

US10/60818) or wild type plant of the same genetic background without an insecticidal trait with activity against *D. virgifera virgifera*. Fifteen individual hybrid corn seed (of each type) were planted into 3.78 L plastic pots and maintained in the greenhouse (80° F., 15:9 L:D) and watered as needed. When the plants reached the V2 leaf stage they were infested with 100 non-diapausing *D. virgifera virgifera* eggs. Plants were monitored daily and the assay ended 14 days after the appearance of the first beetle. The number of adult *D. virgifera virgifera* that emerged from each pot was determined in the GH in a similar manner as described by Meihls et al. (2008) *PNAS* 105: 19177-19182. In those bioassays were adult emergence was not quantified; the assay was evaluated at first beetle emergence. The plants were severed above the soil line and the root ball was then washed and the node-injury-score (CRWNIS) determined (Oleson et al. 2005, *Journal of Economic Entomology* 98: 1-8.) (Table 4). Predicted CRWNIS score and adult emergence were calculated as in Example 2.

TABLE 4

| STRAIN | WT CRWNIS SCORE | DP-4114 CRWNIS SCORE | WT ADULT EMERGENCE | DP-4114 ADULT EMERGENCE |
|---|---|---|---|---|
| 15013-1 @ ~1 x $10^7$/ seed with Gum Arabic | 0.53 | 0.25 | 1.19 | 0.42 |
| 15013-1 @ ~1 x $10^8$/ seed with Gum Arabic | 0.61 | 0.24 | 1.31 | 0.43 |
| 15013-1 @ ~1 x $10^7$/ seed with Gum Arabic & Seed Applied Chemistry | 0.65 | 0.19 | 1.06 | 0.13 |
| 15013-1 @ ~1 x $10^8$/ seed Gum Arabic & Seed Applied Chemistry | 0.52 | 0.17 | 1.07 | 0.65 |
| Gum Arabic Control | 0.91 | 0.30 | 1.12 | 0.21 |
| Gum Arabic & Seed Applied Chemistry Control | 0.55 | 0.17 | 0.66 | 0.18 |

Seed Treatment Results

Seed treatment application of strain 15013-1 lowered the amount of root damage caused by *D. virgifera virgifera* on both corn genotypes when applied alone or in combination with chemical seed treatments. The amount of *D. virgifera virgifera* feeding in both of the seed treatment greenhouse experiments was light. As a result, the amount of insect feeding was highest on the corn genotype without an insecticidal trait which allowed for the impact of each seed treatment evaluated being the most apparent (Table 4). Strain 15013-1 applied alone or in combination with chemical seed treatment reduced the amount of *D. virgifera virgifera* larval feeding (Table 4). The impact of biological seed treatment on adult emergence was more subtle (Table 4). The experimental application of fungal spores to corn seed in this example using 10% gum arabic and the resulting performance compared to the superior performance observed in Example 6 (Table 7) are likely influenced by the use of commercial seed treatment equipment and commercial polymers which result in more uniform and consistent application of the fungal spores to the corn seed.

Example 5

Soil Incorporation Bioassay Methodology

Whole plant greenhouse bioassays were conducted of the most efficacious entomopathogenic fungal strains identified in the laboratory bioassays. Fungal strains were incorporated immediately prior to planting into a 50:50 blend of a commercial potting soil and topsoil at a rate equivalent to a field application of $2\times10^{13}$ CFUs/acre. A negative control treatment consisted of soil not amended with fungal spores. The experiment was a complete factorial design with two factors (fungal strain and genotype). Seed used consisted of a pre-commercial DuPont Pioneer corn hybrid either with an insecticidal trait, DP-4114 (DP-4114, U.S. Pat. No. 8,575, 434), DP-4114 x MIR604 (DP-4114, U.S. Pat. No. 8,575, 434), MIR604 (U.S. Pat. No. 8,884,102) or wild type plants of the same genetic background without an insecticidal trait with activity against *D. virgifera virgifera*. Fifteen individual hybrid corn seed (of each type) were planted into 3.78 L plastic pots and maintained in the greenhouse (80° F., 15:9 L:D) and watered as needed. When the plants reached the V2 leaf stage they were infested with 100 non-diapausing *D. virgifera virgifera* eggs. Plants were monitored daily and the assay ended 14 days after the appearance of the first beetle. The number of adult *D. virgifera virgifera* that emerged from each pot was determined in the GH in a similar manner as described by Meihls et al. (2008) *PNAS* 105: 19177-19182. In those bioassays were adult emergence was not quantified; the assay was evaluated at first beetle emergence. At the conclusion of the assay, the plants were severed above the soil line and the total number of adults present counted (Table 5). The root ball was then washed and the node-injury-score (CRWNIS) determined (Oleson et al. 2005, *Journal of Economic Entomology* 98: 1-8.) (Table 6). The predicted CRWNIS score and adult emergence were calculated as in Example 2.

TABLE 5

| STRAIN | WT ADULT EMERGENCE* | DP-4114 ADULT EMERGENCE* | DP-4114xMIR604 ADULT EMERGENCE* | MIR604 ADULT EMERGENCE* |
|---|---|---|---|---|
| 15013-1 | 4.91a | 4.44a | 4.18a | 2.45a |
| 3213-1 | 4.61a | 7.77b | 5.10a | 7.04a |
| 23013-3 | N/A | N/A | N/A | N/A |
| Negative Control | 7.18b | 9.76b | 8.64b | 10.75b |

*Pair-wise comparisons were made comparing each fungal strain to the negative control given each genotype. A Dunnett multiplicity adjustment was used and adjusted p-values were considered statistically significant if less than 0.05. Means from the same GH bioassay with different letters ("a" or "b") (CRWNIS or Adult Emergence) within a corn hybrid genotype (WT or DP-4114) are significantly different ($P < 0.05$).

TABLE 6

| STRAIN | WT CRWNIS SCORE* | DP-4114 CRWNIS SCORE* | DP-4114xMIR604 CRWNIS SCORE* | MIR604 CRWNIS SCORE* |
|---|---|---|---|---|
| 15013-1 | 0.88a | 0.20a | 0.07b | 0.19a |
| 3213-1 | 0.85a | 0.25a | 0.03a | 0.36a |
| 23013-3 | N/A | N/A | N/A | N/A |
| Negative Control | 1.47b | 0.56b | 0.18b | 0.73b |

*Pair-wise comparisons were made comparing each fungal strain to the negative check given each genotype. A Dunnett multiplicity adjustment was used and adjusted p-values were considered statistically significant if less than 0.05. Means from the same GH bioassay with different letters ("a" or "b") (CRWNIS or Adult Emergence) within a corn hybrid genotype (WT, DP-4114, or DP4114*MIR604, or MIR604) are significantly different ($P < 0.05$).

Bioassay Results

All entomopathogenic fungal strains evaluated in the greenhouse bioassay significantly reduced the amount of root damage on all genotypes of hybrid corn evaluated, with the exception of 15013-1 when applied to DP-4114xMIR604. However, 15013-1 did reduce root feeding damage by over 50% relative to the DP-4114xMIR604 pyramided trait product alone. The efficacy provided by each of the entomopathogenic fungi when incorporated at planting was additive with no significant interaction in terms of insect efficacy when used with or without an insecticidal trait. All fungal strains significantly reduced the number of adult *D. virgifera virgifera* beetles that emerged when incorporated into the soil at planting on all of the hybrid corn genotypes evaluated, with the exception of 3213-1 when applied to DP-4114 alone. However, 3213-1 did reduce the number of emerging adults by over 20% relative to DP-4114 alone. The reduction in adult beetle emergence provided by each of the entomopathogenic fungi when incorporated at planting was additive with no significant interaction when used with or without an insecticidal trait. The use of these fungal strains provided significant level of root protection and reductions in adult emergence as a result of direct mortality against *D. virgifera virgifera* indicating that these fungi are important new tools for use in the development of integrated pest management programs against this insect. In one aspect, the strains may be used to increase the durability of an insecticidal trait.

Example 6

Commercial Seed Treatment Bioassay Methodology

Whole plant greenhouse bioassays were conducted of the entomopathogenic fungal strains identified in Example 1. Fungal strains were applied as biological seed treatments at a target concentration of $1\times10^6$-$1\times10^7$ CFUs/seed along with standard commercial seed-applied insecticides (thiamethoxam and chlorantraniliprole), fungicides (azoxystrobin, fludioxonil, thiabendazole, metalaxyl and tebuconazole) and polymers. Conidia spores were applied as an aqueous liquid formulation or sequentially as dry conidia spores with a seed treatment polymer to previously chemically treated seed. Both formulations of fungal spores and all seed applied chemistries were applied using a commercial bowl treater. Seed were planted into a 50:50 blend of a commercial potting soil and topsoil. A negative control treatment consisted of seed without fungal spores but treated with the same standard and commercially available seed applied insecticides, fungicides, colorants, biologicals, and polymers. The experiment was a complete factorial design with two factors (fungal strain and genotype). Seed used consisted of a pre-commercial DuPont Pioneer corn hybrid either with an insecticidal trait DP-4114 (DP-4114, PCT/US10/60818) or wild type plants of the same genetic background without an insecticidal trait with activity against *D. virgifera virgifera*. Fifteen individual hybrid corn seed (of each type) were planted into 3.78 L plastic pots and maintained in the greenhouse (80° F., 15:9 L:D) and watered as needed. When the plants reached the V2 leaf stage they were infested with 100 non-diapausing *D. virgifera virgifera* eggs. Plants were monitored daily and the assay ended 14 days after the appearance of the first beetle. The number of adult *D. virgifera virgifera* that emerged from each pot was determined in the GH in a similar manner as described by Meihls et al. (2008) *PNAS* 105: 19177-19182. In those bioassays were adult emergence was not quantified; the assay was evaluated at first beetle emergence. At the conclusion of the assay, the plants were severed above the soil line and the total number of adults present counted (Table 7). The root ball was then washed and the node-injury-score (CRWNIS) determined (Oleson et al. 2005, *Journal of Economic Entomology* 98: 1-8.) (Table 7).

TABLE 7

| STRAIN | FORMULATION | WT ADULT EMERGENCE* | DP-4114 ADULT EMERGENCE* | WT CRWNIS SCORE* | DP-4114 CRWNIS SCORE* |
|---|---|---|---|---|---|
| 15013-1 | Liquid | 8.32 | 6.65 | 0.56a | 0.12a |
| 3213-1 | Liquid | 6.99 | 6.99 | 0.60a | 0.13a |
| 23013-3 | Liquid | 10.26 | 7.72 | 0.44a | 0.16a |
| 15013-1 | Sequential | 7.84 | 7.18 | 0.57a | 0.19a |
| 3213-1 | Sequential | 8.06 | 8.12 | 0.56a | 0.16a |
| 23013-3 | Sequential | 9.22 | 7.13 | 0.49a | 0.25a |
| Negative Control | N/A | 10.36 | 7.89 | 0.82b | 0.41b |

*Pair-wise comparisons were made comparing each fungal strain to the negative control given each genotype. A Dunnett multiplicity adjustment was used and adjusted p-values were considered statistically significant if less than 0.05. Means from the same GH bioassay with different letters ("a" or "b") (CRWNIS or Adult Emergence) within a corn hybrid genotype (WT or DP-4114) are significantly different ($P < 0.05$).

Bioassay Results

All entomopathogenic fungal strains, in both formulation types, evaluated in the greenhouse bioassay significantly reduced the amount of root damage on both WT and DP-4114 traited hybrid corn when delivered as a seed treatment along with conventional seed applied chemistries. This was unexpected as the growth and germination of *Metarhizium* spp. are significantly slowed by all the corn seed applied fungicides with activity against filamentous fungi as in Example 8. The efficacy provided by each of the entomopathogenic fungi when applied as a seed treatment were additive with no significant interaction in terms of insect efficacy when used with or without DP-4114. The use of these fungal strains provided significant levels of additive root protection and reduced the number of adults that emerged from each pot on average. These data indicate that these fungi are important new tools for use in the development of integrated pest management programs against *Diabrotica virgifera virgifera* and can be effectively delivered as a seed treatment in multiple types of formulations, even in the presence of a fungicide whether premixed as a liquid with the fungicide or applied to seed already treated with a fungicide.

Example 7

Soil Incorporation Bioassay Methodology

Whole plant greenhouse bioassays were conducted of efficacious entomopathogenic fungal strains identified in the laboratory bioassays. Fungal strains were incorporated immediately prior to planting into a 50:50 blend of a commercial potting soil and topsoil at a rate equivalent to a field application of $2\times10^{13}$ CFU/acre. A negative control treatment consisted of soil not amended with fungal spores. The experiment was a complete factorial design with two factors (fungal strain and genotype). Seed used consisted of a corn hybrid either with an insecticidal trait, RyanR (DvSSJ1, 2014/0275208 and US2015/0257389), IPD072 (PCT/US14/55128) or plants of the same genetic background without an insecticidal trait activity against *D. virgifera virgifera*. Fifteen individual hybrid corn seed (of each type) were planted into 3.78 L plastic pots and maintained in the greenhouse (80° F., 15:9 L:D) and watered as needed. When the plants reached the V2 leaf stage they were infested with 100 non-diapausing *D. virgifera virgifera* eggs. Plants were monitored daily and the assay ended 14 days after the appearance of the first beetle. The number of adult *D. virgifera virgifera* that emerged from each pot was determined in the GH in a similar manner as described by Meihls et al. (2008) *PNAS* 105: 19177-19182. At the conclusion of the assay, the plants were severed above the soil line and the total number of adults present counted (Table 8). The root ball was then washed and the node-injury-score (CRWNIS) determined (Oleson et al. 2005, *Journal of Economic Entomology* 98: 1-8.) (Table 8). The predicted CRWNIS score and adult emergence were calculated as in Example 2.

TABLE 8

| STRAIN | WT CRWNIS SCORE* | DvSSJ1 CRWNIS SCORE* | IPD072 CRWNIS SCORE* |
|---|---|---|---|
| 15013-1 | 0.30a | 0.05a | 0.00a |
| 3213-1 | 0.34a | 0.16b | 0.00a |
| 23013-3 | 0.46a | 0.17b | 0.00a |
| Negative Control | 1.10b | 0.12b | 0.08b |

| STRAIN | WT ADULT EMERGENCE* | DvSSJ1 ADULT EMERGENCE* | IPD072 ADULT EMERGENCE* |
|---|---|---|---|
| 15013-1 | 10.47a | 5.60a | 8.07a |
| 3213-1 | 8.43a | 8.33a | 9.21b |
| 23013-3 | 12.42a | 8.29a | 11.30b |
| Negative Control | 18.13b | 11.26b | 10.27b |

*Pair-wise comparisons were made comparing each fungal strain to the negative control given each genotype. A Dunnett multiplicity adjustment was used and adjusted p-values were considered statistically significant if less than 0.05. Means from the same GH bioassay with different letters ("a" or "b") (CRWNIS or Adult Emergence) within a corn hybrid genotype (WT, DvSSJ1, or IPD072) are significantly different ($P < 0.05$).

Bioassay Results

All entomopathogenic fungal strains evaluated in the greenhouse bioassay significantly reduced the amount of root damage on all genotypes of hybrid corn evaluated, with the exception of 3213-1 and 23013-3 strains when applied to DvSSJ1. The efficacy provided by each of the entomopathogenic fungi when incorporated at planting was additive with no significant interaction in terms of insect efficacy when used with or without an insecticidal trait. All fungal strains significantly reduced the number of adult *D. virgifera virgifera* beetles that emerged when incorporated into the soil at planting on all of the hybrid corn genotypes evaluated, with the exception of 3213-1 and 23013-3 strains when applied to IPD072. However, 3213-1 did reduce the number of emerging adults by 10% relative to IPD072 alone. The reduction in adult beetle emergence provided by each of the entomopathogenic fungi when incorporated at planting was additive with no significant interaction when used with or without an insecticidal trait. The use of these fungal strains provided significant level of root protection and reductions in adult emergence as a result of direct mortality against *D. virgifera virgifera* with non-*Bacillus thuringiensis* based protein and RNAi insecticidal traits. The results indicate that the strains may be used to increase the durability of non-*Bacillus thuringiensis* insecticidal traits.

Example 8

Determination of Fungicide Sensitivity in *Metarhizium* spp.

Conidia of *Metarhizium robertsii* (15013-1) and *Metarhizium robertsii* (23013-3) were produced by growing the fungus on potato dextrose agar plates for 1-2 weeks at 23° C. under continuous illumination from fluorescent lights. Conidia were harvested from the plate in water containing Tween-20 (0.01%) and counted using a hemacytometer. Fungicide sensitivity was determined by mixing 5,000 conidia in 0.5 ml of YMA (2 g yeast extract, 4 g malt extract per liter) liquid media containing varying concentrations of commercially available fungicides active against filamentous fungi in a 24 well plate. Plates were incubated for ~24 hour at 26° C. and then growth was assessed by visual observation with a stereomicroscope.

TABLE 9

15013-1 (Conidia in control, "no compound" (NC) showed single long germ tubes, >20X the diameter of the germ tube. Fungal growth completely filled the well.)

| | Fungicide Concentration | | |
|---|---|---|---|
| | 3 uM | 10 uM | 30 uM |
| Azoxystrobin | ++ | + | − |
| Fludioxonil | + | + | + |
| Thiabendazole | ++++ | ++++ | ++++ |

"++++" means growth of about 50% or more compared to a control without any fungicide.
"+++" means growth of about 30% or about 70% inhibition compared to a control without any fungicide.
"++" means growth of about 20% or about 80% inhibition compared to a control without any fungicide.
"+" means growth of about 10% or about 90% inhibition compared to a control without any fungicide.
"−" means no growth or complete inhibition comparted to a control without any fungicide.

TABLE 10

| 23013-3 (Conidia in control, "no compound" (NC) conidia showed long germ tubes, >20X the diameter of the germ tube. Fungal growth almost completely filled the well.) | | | |
|---|---|---|---|
| | Fungicide Concentration | | |
| | 3 uM | 10 uM | 30 uM |
| Azoxystrobin | + | − | − |
| Fludioxonil | + | + | + |
| Thiabendazole | +++ | ++++ | ++++ |

"++++" means growth of about 50% or more compared to a control without any fungicide.
"+++" means growth of about 30% or about 70% inhibition compared to a control without any fungicide.
"++" means growth of about 20% or about 80% inhibition compared to a control without any fungicide.
"+" means growth of about 10% or about 90% inhibition compared to a control without any fungicide.
"−" means no growth or complete inhibition comparted to a control without any fungicide.

Results

*M. anisopliae* and *M. robertsii* are sensitive to the active ingredients in commercially available fungicidal seed treatment with known activity against filamentous fungi (Table 9 and Table 10).

Example 9

Selection of *Metarhizium* Strains Resistant to Fungicides

Isolation of fungal strains resistant to fungicides takes advantage of the fact that resistance to fungicides most often results from a single point mutation in the gene that encodes that protein targeted by the fungicide. This point mutation results in an amino acid change in the protein which decreases fungicide binding to the target protein and confers the strain harboring this mutation with a high level of resistance to the fungicide. Fungal isolates resistant to fungicides are selected in the following manner. Conidia of *Metarhizium* spp. are produced by growing the fungus on potato dextrose agar plates for 1-2 weeks at 23° C. under continuous illumination from fluorescent lights. Conidia are harvested, counted and diluted to 10,000,000/ml in water. Conidia are then exposed to a mutagen for varying lengths of time. For example, conidia may be exposed to UV light for 0.5-3 minutes or to ethyl methanesulfonate (2-3% for 30-60 minutes). After exposure to the mutagen, conidia are allowed to recover and express the resistant form of the protein by embedding them in molten YMA low melting point agarose. Plates are incubated for about 24 hours at 26° C. After the recovery period, conidia are exposed to the selective compound (e.g. azoyxstrobin, fludioxonil, or thiabendazole) by overlaying the conidia with a second layer of YMA agarose containing the selective fungicide. The fungicide is used at a concentration about 10-fold higher than the minimal concentration required to inhibit fungal growth. Plates containing conidia growing in the presence of the fungicide are then incubated for 3-10 days and monitored periodically for the presence of fungal growth. When growing colonies are found they are aseptically removed from the selection plates and transferred to new growth media. After growth on media without the fungicide, the isolates are tested for fungicide resistance by exposing them to various concentrations of fungicides and their sensitivity compared to the wild-type strain. A selected strain will be expected to show greater efficacy in inhibiting a plant pathogen, pest, or insect in the presence of a seed treatment comprising a fungicide or other fungicidal application to a plant or plant part.

Example 10

Twelve sites tested were located in commercial maize-growing regions of North America where infestations of *Diabrotica virgifera virgifera* (WCRW) and *Diabrotica barberi* (NCRW) occur. Locations planted include: Brookings, S.D.; Goodland, Ind.; Fowler, Ind.; (2) Johnston, Iowa; Seymour, Ill.; Mankato, Minn.; York, Nebra.; Grafton, Nebra.; and Rochelle, Ill.

The experimental units comprised seed treated as in Example 6 and were planted in a single-row plot of maize 10 feet in length with a row spacing of 30 inches. Four replications per treatment arranged in a split-plot design with corn genotype as the main plot and seed treatment as the subplot. Each experimental unit was infested with approximately 750 western corn rootworm eggs at the early vegetative stage and 2 plants/experimental unit were dug and assigned a CRWNIS. Two untraited corn hybrids were used. The fungal strains were applied to the seed along with standard commercial seed-applied insecticides (thiamethoxam and chlorantraniliprole), fungicides (azoxystrobin, fludioxonil, thiabendazole, metalaxyl and tebuconazole) and polymers. The rate of each insecticide (250 mg active ingredient/seed) was the labeled rate for control of certain secondary insect pests of maize. However, at the rates used, neither standard insecticidal seed treatment provided activity against corn rootworm. The positive seed treatment control for CRW control was PonchoVotivo 1250®. At the conclusion of the field experiment, the plants were severed above the soil line, the root ball washed and the CRWNIS determined (Oleson et al. 2005, *Journal of Economic Entomology* 98: 1-8.).

Statistical Analysis:

ASReml software version 3.0, accessed with TTRS (Transgenic Trait Research System), was used to fit linear mixed models and to test contrasts of interest. In order to better meet model assumptions, CRWINS observed values were transformed, using a square root transformation, prior to analysis. Best linear unbiased estimates were reported for seed treatments following back transformation. Pair-wise comparisons were made among seed treatments where a difference was considered statistically significant if the p-value of the difference test was less than 0.05.

Results

When evaluating actives for their efficacy against WCRW and NCRW; the most informative locations are those with high insect pressure (>1.5 nodes of CRW feeding). When the two high pressure locations from the 2015 field trials (Johnston, Iowa and York, Nebra.) were pooled for analysis, the liquid formulation of the 3213-1 strain applied as a seed treatment to the untraited genotype provided statistically significant root protection compared to the negative control at the 0.05 level of confidence (FIG. 1). The level of control from the liquid formulation of 3213-1 in the untraited genotype under high corn rootworm pressure was statistically similar to the efficacy provided by the current commercial chemical standard seed treatment (Poncho Votivo 1250®) for corn rootworm control (FIG. 1). The relative overall performance of all of the fungal strains in both formulations (liquid and dry sequential) improved root protection on untraited hybrids with approximately 0.25 node improvement relative to the negative control.

All publications, patents and patent applications mentioned in the specification indicate the level of those skilled in the art to which this disclosure pertains. All publications, patents and patent applications are incorporated by reference to the same extent as if each individual publication, patent or patent application was specifically and individually indicated to be incorporated by reference.

Although the foregoing disclosure has been described in some detail by way of illustration and example for purposes of clarity of understanding, certain changes and modifications may be practiced within the scope of the appended claims.

What is claimed is:

1. A treated seed composition comprising a seed, wherein the seed is coated with a seed additive and a fungal entomopathogen selected from the group consisting *Metarhizium robertsii* 15013-1 (deposited under NRRL accession number 67073), *Metarhizium robertsii* 23013-3 (deposited under NRRL accession number 67075), and *Metarhizium anisopliae* 3213-1 (deposited under NRRL accession number 67074), and wherein the composition comprises at least about $1\times10^2$ CFUs of the fungal entomopathogen.

2. The composition of claim 1, wherein the seed is a genetically modified or transgenic seed.

3. The composition of claim 2, wherein the genetically modified or transgenic seed comprises an insecticidal trait.

4. The composition of claim 3, wherein the insecticidal trait controls a *Coleopteran* plant pest.

5. The composition of claim 4, wherein the *Coleopteran* plant pest comprises a *Diabrotica virgifera virgifera* plant pest.

6. The composition of claim 2, wherein the insecticidal trait comprises an event selected from the group consisting of event MON863, event MIR604, event 5307, event DAS-59122, event DP-4114, event MON 87411, and event MON88017.

7. The composition of claim 3, wherein the genetically modified or transgenic seed further comprises an additional herbicide tolerance trait.

8. The composition of claim 1, wherein the composition further comprises a biocontrol agent selected from the group consisting of a bacteria, a fungus, a yeast, a protozoa, a virus, an entomopathogenic nematode, a botanical extract, a protein, a nucleic acid, a secondary metabolite, and an innoculant.

9. The composition of claim 1, wherein the composition further comprises an agrochemically active compound selected from the group consisting of an insecticide, a fungicide, a bactericide, and a nematicide.

10. The composition of claim 9, wherein the fungicide comprises a fungicide composition selected from the group consisting of azoxystrobin, thiabendazole, fludioxonil, metalaxyl, tebuconazole, prothioconazole, ipconazole, penflufen, and sedaxane.

11. The composition of claim 10, wherein the composition further comprises a compound selected from the group consisting of a safener, a lipo-chitooligosaccharide, a triglucosamine lipoglycine salt, an isoflavone, and a ryanodine receptor modulator.

12. The composition of claim 10, wherein the fungal entomopathogen is resistant to a fungicide.

13. The composition of claim 10, wherein the fungal entomopathogen comprises a spore.

14. The composition of claim 10, wherein the fungal entomopathogen comprises a conidia.

15. The composition of claim 10, wherein the fungal entomopathogen comprises a microsclerotia.

16. A method of increasing resistance of a plant to a plant pathogen, a pest, or an insect comprising providing a seed composition which comprises a seed, wherein the seed is coated with a seed additive and a fungal entomopathogen selected from the group consisting *Metarhizium robertsii* 15013-1 (deposited under NRRL accession number 67073), *Metarhizium robertsii* 23013-3) deposited under NRRL accession number 67075), and *Metarhizium anisopliae* 3213-1 (deposited under NRRL accession number 67074), and wherein the composition comprises at least about $1\times10^2$ CFUs of the fungal entomopathogen.

17. The method of claim 16, further comprising planting the composition.

18. The method of claim 16, wherein the seed is a genetically modified or transgenic seed.

19. The method of claim 18, wherein the genetically modified seed comprises an insecticidal trait.

20. The method of claim 19, wherein the insecticidal trait comprises a Bt trait, a silencing element or a non-Bt insecticidal protein.

21. The method of claim 20, wherein the insecticidal trait is selected from the group consisting of event MON863, event MIR604, event 5307, event DAS-59122, event DP-4114, event MON 87411, and event MON88017.

22. The method of claim 16, wherein the composition further comprises a biocontrol agent selected from the group consisting of a bacteria, a fungus, a yeast, a protozoa, a virus, an entomopathogenic nematode, a botanical extract, a protein, a nucleic acid, a secondary metabolite, and an innoculant.

23. The method of claim 16, wherein the composition further comprises an agrochemically active compound selected from the group consisting of an insecticide, a fungicide, a bactericide, and a nematicide.

24. The method of claim 23, wherein the fungicide comprises a fungicide composition selected from the group consisting of azoxystrobin, thiabendazole, fludioxonil, metalaxyl, tebuconazole, prothioconazole, ipconazole, penflufen, and sedaxane.

25. The method of claim 16, wherein the composition further comprises a compound selected from the group consisting of a safener, a lipo-chitooligosaccharide, a triglucosamine lipoglycine salt, an isoflavone, and a ryanodine receptor modulator.

26. The method of claim 16, wherein the fungal entomopathogen comprises a spore.

27. The method of claim 16, wherein the fungal entomopathogen comprises a conidia.

28. The method of claim 16, wherein the fungal entomopathogen comprises a microsclerotia.

* * * * *